US010941178B2

(12) United States Patent
Sanaie et al.

(10) Patent No.: US 10,941,178 B2
(45) Date of Patent: Mar. 9, 2021

(54) METHOD OF PURIFYING AN ANTIBODY

(71) Applicant: Gilead Sciences, Inc., Foster City, CA (US)

(72) Inventors: Nooshafarin Sanaie, Foster City, CA (US); Brian Kluck, Foster City, CA (US); Andrew Quezada, Foster City, CA (US); Robert vonder Reith, Foster City, CA (US); Chi Tran, Foster City, CA (US); James Woo, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 270 days.

(21) Appl. No.: 15/924,163

(22) Filed: Mar. 16, 2018

(65) Prior Publication Data
US 2018/0265543 A1    Sep. 20, 2018

Related U.S. Application Data

(60) Provisional application No. 62/473,210, filed on Mar. 17, 2017, provisional application No. 62/478,495, filed on Mar. 29, 2017.

(51) Int. Cl.
| | |
|---|---|
| *C07K 1/22* | (2006.01) |
| *C07K 1/36* | (2006.01) |
| *C07K 16/40* | (2006.01) |
| *C07K 1/16* | (2006.01) |
| *C07K 1/18* | (2006.01) |

(52) U.S. Cl.
CPC ............... *C07K 1/22* (2013.01); *C07K 1/165* (2013.01); *C07K 1/18* (2013.01); *C07K 1/36* (2013.01); *C07K 16/40* (2013.01)

(58) Field of Classification Search
CPC .................... C07K 1/22; C07K 1/36
See application file for complete search history.

(56) References Cited

U.S. PATENT DOCUMENTS

| | | | |
|---|---|---|---|
| 8,377,443 B2 | 2/2013 | McCauley et al. | |
| 8,501,916 B2 | 8/2013 | McCauley et al. | |
| 9,120,863 B2 | 9/2015 | McCauley et al. | |
| 9,260,532 B2 | 2/2016 | McCauley et al. | |
| 2006/0269989 A1* | 11/2006 | Miyazaki | C07K 16/468 435/69.1 |
| 2007/0082367 A1* | 4/2007 | Godavarti | C07K 16/18 435/7.2 |
| 2008/0269467 A1* | 10/2008 | Allan | A61P 37/06 530/387.3 |
| 2009/0053324 A1 | 2/2009 | Neuls | |
| 2011/0200606 A1* | 8/2011 | McCauley | A61P 11/00 424/139.1 |
| 2013/0317198 A1* | 11/2013 | Coffman | C07K 1/165 530/387.1 |
| 2015/0140580 A1 | 5/2015 | Smith et al. | |
| 2015/0329588 A1* | 11/2015 | Wang | C07K 1/22 530/388.15 |
| 2016/0251425 A1* | 9/2016 | Ramasubramanyan | C07K 1/22 424/142.1 |

FOREIGN PATENT DOCUMENTS

| | | |
|---|---|---|
| WO | WO-2007/109163 A2 | 9/2007 |
| WO | WO-2009/017833 A2 | 2/2009 |
| WO | WO-2009/035791 A1 | 3/2009 |
| WO | WO-2013/130078 A1 | 9/2013 |
| WO | WO-2015/130813 A1 | 9/2015 |
| WO | WO-2016/153978 A1 | 9/2016 |

OTHER PUBLICATIONS

Shukla et al. "Host cell protein clearance during protein a chromatography: development of an improved column wash step" Biotechnol. Prog. 2008, 24, 1115-1121 (Year: 2008).*
Shukla et al. "Downstream processing of monoclonal antibodies—Application of platform approaches" J of Chromatography B, 848 (2007) 28-39 (Year: 2007).*
Aboulaich, N. et al. (2014, e-pub. Jul. 26, 2014). "A Novel Approach to Monitor Clearance of Host Cell Proteins Associated With Monoclonal Antibodies," *American Institute of Chemical Engineers Biotechnol. Prog.* 30:1114-1124.
Chollangi, S. et al. (2015). Development of Robust Antibody Purification by Optimizing Protein-A Chromatography in Combination With Precipitation Methodologies, *Biotechnology and Bioengineering* 9999:1-13.
Wang, H. et al (Mar. 2008, e-pub. Sep. 19, 2007). "Expression, Purification, and Characterization of an Immunotoxin Containing a Humanized anti-CD25 Single-Chain Fragment Variable Antibody Fused to a Modified Truncated Pseudomonas Exotoxin A", *Protein Expr Purif.* 58(1):140-147.
Zhang, Q. et al. (2016, e-pub. May 6, 2016). "Characterization of the Co-Elution of Host Cell Proteins with Monoclonal Antibodies during Protein A Purification," *American Institute of Chemical Engineers Biotechnol. Prog.* 32:708-717.

(Continued)

*Primary Examiner* — Daniel E Kolker
*Assistant Examiner* — James L Rogers
(74) *Attorney, Agent, or Firm* — Morrison & Foerster LLP

(57) ABSTRACT

The present disclosure relates generally to methods of producing, processing, or purifying antibodies. The present disclosure also relates to methods of producing, processing, or purifying a target antibody from cell cultures to remove host cell proteins.

19 Claims, No Drawings
Specification includes a Sequence Listing.

(56) References Cited

OTHER PUBLICATIONS

International Search Report dated Jun. 14, 2018, for PCT Application No. PCT/US2018/023022, filed on Mar. 16, 2018, 8 pages.
Written Opinion of the International Searching Authority dated Jun. 14, 2018, for PCT Application No. PCT/US2018/023022, filed on Mar. 16, 2018, 12 pages.
International Preliminary Report on Patentability dated Sep. 26, 2019, for PCT Application No. PCT/US2018/023022, filed on Mar. 16, 2018, 11 pages.

* cited by examiner

METHOD OF PURIFYING AN ANTIBODY

CROSS-REFERENCE TO RELATED APPLICATIONS

This application claims priority from U.S. provisional application No. 62/473,210 filed Mar. 17, 2017, U.S. provisional application No. 62/478,495 filed Mar. 29, 2017, the contents of which are incorporated herein by reference in their entirety.

INCORPORATION BY REFERENCE OF SEQUENCE LISTING

The present application is being filed along with a Sequence Listing in electronic format. The content of the following submission on ASCII text file is incorporated herein by reference in its entirety: a computer readable form (CRF) of the Sequence Listing (file name: 616082010800SeqList.txt, date recorded: Mar. 16, 2018, size: 58 KB).

FIELD

The present disclosure relates generally to methods of producing, processing, or purifying antibodies. The present disclosure also relates to methods of producing, processing, or purifying a target antibody from cell cultures to remove host cell proteins.

BACKGROUND

Antibodies, such as monoclonal antibodies (mAbs), are becoming important therapeutic agents in the pharmaceutical industry. Antibody therapeutics are used to treat a wide array of disease indications, including cancer, inflammation, and autoimmune disorders. In general, antibodies are produced in mammalian cell culture to ensure proper folding and post-translational modification, such as glycosylation. Antibodies produced from cell cultures need to be purified from host cell proteins and other impurities in order to be effectively utilized. Methods for purifying antibodies generally involve harvesting and clarifying the cell culture fluid, separating the antibody from the majority of components in the clarified harvested cell culture fluid; purifying the antibody from residual host cell impurities and aggregates; and placing the antibody into an appropriate carrier for maximum stability and shelf life.

Current methods for purifying antibodies are often cumbersome, costly and may not remove host cell impurities in the cell culture, including those copurified with the antibodies, which makes the downstream process challenging. Accordingly, there is a need for methods for purifying antibodies suitable for pharmaceutical use.

BRIEF SUMMARY

In one aspect, provided herein is a method for producing, processing, or purifying an antibody from a host cell culture fluid (HCCF) comprising the antibody. The method comprises loading a host cell culture fluid or a solution comprising a target antibody onto a protein A chromatography matrix, washing the matrix with at least one wash solution comprising urea and eluting with an elution buffer to obtain the target antibody. The wash solution may further comprise up to 1000 mM sodium chloride and may be at a pH from about 5.0 to about 8.5. In another aspect, the wash solution may further comprise up to about 1500 mM sodium chloride and may be at a pH from about 5.0 to about 8.5. In additional aspects, the methods provided herein may further comprise washing the protein A chromatography matrix with at least one additional wash solution that comprises at least one additive, such as arginine, guanidine, sodium chloride, or caprylate. In additional aspects, the method further comprises one or more depth filtration steps, which comprises COHC and XOHC depth filters or COHC depth filter and a filter capsule, and optionally a mixed-mode chromatography step. In another aspect, provided herein is a method for processing or purifying a target antibody from a HCCF or a solution comprising the target antibody, wherein the method comprises a protein A affinity chromatography step, a low pH viral inactivation step, one or more depth filtration steps, and a mixed-mode chromatography step. In some aspects, the methods provided herein reduce the level of host cell protein (HCP) in the filtrate pool and/or the level of product-related impurities in the filtrate pool.

Accordingly, the present disclosure provides a method for purifying an antibody from a host cell culture fluid comprising the antibody, the method comprising: a) loading the host cell culture fluid onto protein A chromatography matrix to obtain a loaded matrix; b) washing the loaded matrix with at least one wash solution, wherein the at least one wash solution comprises at least one urea wash solution comprising from about 500 mM to about 8000 mM urea; and c) eluting the antibody with an elution buffer to obtain protein A purified antibody. The at least one wash solution may further comprise at least one additional wash solution comprising one or more of arginine, guanidine, sodium chloride (NaCl), and caprylate. In an embodiment, the at least one additional wash solution comprises at least one arginine wash solution comprising from about 100 mM to 1000 mM arginine. In an embodiment, the at least one arginine wash solution comprises about 800 mM arginine. In another embodiment, the at least one additional wash solution comprises at least one guanidine wash solution comprising from about 500 mM to about 1000 mM guanidine. In some embodiments, the at least one guanidine wash solution comprises about 1000 mM guanidine. In another embodiment, the at least one additional wash solution comprises at least one NaCl wash solution comprising from about 500 mM to about 1000 mM NaCl. In a certain embodiment, the at least one NaCl wash solution comprises about 500 mM NaCl. In another embodiment, the at least one additional wash solution comprises at least one caprylate wash solution comprising from about 1 mM to about 50 mM caprylate. In a certain embodiment, the at least one caprylate wash solution comprises about 25 mM caprylate.

In an embodiment, the at least one wash solution comprises at least one arginine wash solution comprising from about 100 mM to 1000 mM arginine. In an embodiment, the at least one arginine wash solution comprises about 800 mM arginine. In another embodiment, the at least one wash solution comprises at least one guanidine wash solution comprising from about 500 mM to about 1000 mM guanidine. In some embodiments, the at least one guanidine wash solution comprises about 1000 mM guanidine. In another embodiment, the at least one wash solution comprises at least one NaCl wash solution comprising from about 500 mM to about 1500 mM NaCl. In a certain embodiment, the at least one NaCl wash solution comprises about 500 mM NaCl. In another embodiment, the at least one wash solution comprises at least one caprylate wash solution comprising from about 1 mM to about 50 mM caprylate. In a certain embodiment, the at least one wash solution comprises at least one wash solution comprising from about 100 mM to 1000 mM arginine, from about 500 mM to about 1000 mM guanidine, from about 500 mM to about 1500 mM NaCl, from about 1 mM to about 50 mM caprylate, or combination thereof. In a certain embodiment, the at least one wash solution comprises a urea wash solution, an arginine wash solution, a guanidine wash solution, an NaCl wash solution, a capyrlate wash solution, or combination thereof. In a certain embodiment, the at least one caprylate wash solution comprises about 25 mM caprylate. In an embodiment, the at least one additional wash solution is at a pH from about 5.0 to about 8.5. In a certain embodiment, the at least one additional wash solution is at a pH of about 7.7. In an embodiment, the at least one urea wash solution comprises from about 2000 mM to about 8000 mM urea. In a certain embodiment, the at least one urea wash solution comprises from about 4000 mM to about 8000 mM urea. In a certain embodiment, the at least one urea wash solution comprises about 4000 mM urea. In another embodiment, the at least one urea wash solution comprises about 6000 mM urea.

In another embodiment, the at least one urea wash solution further comprises from about 500 mM to about 1500 mM NaCl. In a certain embodiment, the at least one urea wash solution comprises about 500 mM NaCl. In another embodiment, the at least one urea wash solution comprises about 1000 mM NaCl. In an embodiment, the elution buffer comprises from about 5 mM to about 65 mM acetic acid. In a certain embodiment, the at least one urea wash solution comprises 4000 mM urea and 1000 mM NaCl, and the elution buffer comprises 40 mM acetic acid. In an embodiment, the at least one urea wash solution is at a pH from about 5.0 to about 8.5. In a certain embodiment, the at least one urea wash solution is at a pH of about 7.7. In an embodiment, the elution buffer is at a pH of about 2.5 to about 3.5. In a certain embodiment, the elution buffer is at a pH of about 3.1. In an embodiment, the washing the loaded matrix step is carried out at a flow rate of about 50 cm/hr to about 400 cm/hr. In a certain embodiment, the washing the loaded matrix step is carried out at a flow rate of about 100 cm/hr. In an embodiment, the washing the loaded matrix step is repeated at least one, two, three, or four times. In certain embodiment, the washing step is repeated at least three times with the same wash solution. In some embodiments, the method further comprises subjecting the protein A purified antibody to viral inactivation. In a certain embodiment, the viral inactivation is conducted at a pH below 4.0 for at least 30 minutes. In a certain embodiment, the pH for the viral inactivation step is from about 3.4 to about 3.8. In some embodiments, the pH of the protein A purified antibody is adjusted to a pH from about 5.0 to about 6.5 following the viral inactivation step. In a certain embodiment, the pH of the protein A purified antibody is adjusted to about 6.0 following the viral inactivation step.

In some embodiments, the method further comprises subjecting the protein A purified antibody to depth filtration step. In a certain embodiment, the depth filtration step comprises at least one depth filtration step. In a certain embodiment, the depth filtration step comprises a filter selected from the group consisting of a COHC depth filter, a XOHC depth filter, a synthetic hybrid depth filter (e.g., Emphaze™), and combinations thereof. In some embodiments, the method further comprises a membrane filtration step.

In some embodiments, the method further comprises loading the protein A purified antibody onto a cation exchange chromatography matrix to obtain a cation exchange purified antibody. In a certain embodiment, the cation exchange chromatography step comprises a matrix selected from the group consisting of a Capto™ S matrix, an SP Sepharose FF® matrix, an S Ceramic HyperD™ matrix, a HyperCel™ Star CEX matrix, and a Poros® XS matrix.

In some embodiments, the method further comprises loading the protein A purified antibody onto a mixed-mode chromatography matrix to obtain a mixed-mode purified antibody. In some embodiments, the method further comprises loading the cation exchange purified antibody onto a mixed-mode chromatography matrix to obtain a mixed-mode purified antibody. In some embodiments, the mixed-mode chromatography step comprises anion exchange and hydrophobic interaction mechanisms. In certain embodiments, the mixed-mode chromatography step comprises a matrix selected from the group consisting of a Capto Adhere matrix, a Capto Adhere ImpRes matrix, a Capto MMC matrix, and a Capto MMC ImpRes matrix.

In some embodiments, the method further comprises subjecting the protein A purified antibody to a viral filtration process to obtain a viral filtered purified antibody. In some embodiments, the method further comprises subjecting the cation exchange purified antibody to a viral filtration process to obtain a viral filtered purified antibody. In some embodiments, the method further comprises subjecting the mixed-mode purified antibody to a viral filtration process to obtain a viral filtered purified antibody. In some embodiments, the method further comprises subjecting the protein A purified antibody to ultrafiltration and diafiltration. In some embodiments, the method further comprises subjecting the cation exchange purified antibody to ultrafiltration and diafiltration. In some embodiments, the method further comprises subjecting the mixed-mode purified antibody to ultrafiltration and diafiltration. In some embodiments, the method further comprises subjecting the viral filtered purified antibody to ultrafiltration and diafiltration.

Also provided is a method for purifying an antibody from a host cell culture fluid comprising the antibody, the method comprising: a) loading the host cell culture fluid onto a protein A or protein L chromatography matrix to obtain a loaded matrix; b) washing the loaded matrix with at least one wash solution, wherein the at least one wash solution comprises at least one urea wash solution comprising from about 4000 mM to about 8000 mM urea; and c) eluting the antibody using a pH gradient-based elution or a multi-step elution to obtain purified antibody. In some embodiments, the chromatography matrix is a protein A chromatography matrix. In other embodiments, the chromatography matrix is a protein L chromatography matrix. In some embodiments, eluting the antibody utilizes multi-step elution. In other embodiments, eluting the antibody utilizes pH gradient-based elution. In some embodiments, the antibody is processed through at least two successive cycles of multi-step elution. In some embodiments, the antibody is processed through at least two successive cycles of pH gradient-based elution.

Also provided is a method for purifying an antibody from a host cell culture fluid comprising the antibody, the method comprising: a) loading the host cell culture fluid onto protein A chromatography matrix to obtain a loaded matrix; b) washing the loaded matrix with at least one wash solution, wherein the at least one wash solution comprises from about 4000 mM to about 6000 mM urea and from about 500 mM to about 1500 mM NaCl and is at a pH of about 7.7 to about 8.2; c) eluting the antibody with an elution buffer to obtain protein A purified antibody; and d) filtering the protein A purified antibody by depth filtration, wherein the depth filtration comprises a depth filter selected from the group consisting of a COHC depth filter, a XOHC depth filter, a synthetic hybrid depth filter (e.g., Emphaze™), and combinations thereof.

Also provided for is a method for purifying, producing, processing, or isolating an antibody from a mixture comprising the antibody, the method comprising: a) loading the mixture onto protein A chromatography; b) washing the chromatography with at least one wash solution, wherein the at least one wash solution comprises from about 500 mM to about 8000 mM urea;

and c) eluting with an elution buffer to obtain the antibody. The at least one wash solution may further comprise arginine, guanidine, sodium chloride (NaCl), caprylate, or combinations thereof. In a certain embodiment, the at least one wash solution comprises from about 100 mM to 1000 mM arginine, from about 500 mM to about 1000 mM guanidine, from about 500 mM to about 1500 mM NaCl, from about 1 mM to about 50 mM caprylate, or combination thereof. In an embodiment, the at least one wash solution is at a pH from about 5.0 to about 8.5. In an embodiment, the elution buffer comprises from about 5 mM to about 65 mM acetic acid. In a certain embodiment, the at least one urea wash solution is at a pH of about 7.7. In an embodiment, the elution buffer is at a pH of about 2.5 to about 3.5. In an embodiment, the washing step is carried out at a flow rate of about 50 cm/hr to about 400 cm/hr. In an embodiment, the washing step is repeated at least one, two, three, or four times. In some embodiments, the method further comprises viral inactivation. In a certain embodiment, the viral inactivation is conducted at a pH below 4.0 for at least 30 minutes. In some embodiments, the method further comprising depth filtration, membrane filtration, a cation exchange chromatography, a mixed-mode chromatography, ultrafiltration, diafiltration, or combination thereof. In a certain embodiment, the method further comprises a filtering step using depth filtration. In a certain embodiment, the depth filtration comprises a filter selected from the group consisting of a COHC depth filter, a XOHC depth filter, a synthetic hybrid depth filter (e.g., Emphaze™), or combinations thereof.

Also provided is a method for producing, purifying, processing, or isolating an antibody from a host cell culture fluid comprising the antibody, the method comprising: a) loading the host cell culture fluid onto a protein A or protein L chromatography to obtain a loaded matrix; b) washing the matrix with at least one urea wash solution, wherein the at least one urea wash solution comprises from about 4000 mM to about 8000 mM urea to obtain a protein A purified antibody or protein L purified antibody; and c) subjecting a protein A purified antibody or protein L purified antibody to a pH gradient-based elution or a multi-step elution to obtain the antibody. In some embodiments, the host cell culture is loaded onto protein A chromatography, and the at least one urea wash solution comprises from about 4000 mM to about 6000 mM urea and from about 500 mM to about 1500 mM NaCl and is at a pH of about 7.7 to about 8.2. In some embodiments, the method further comprises filtering the protein A purified antibody by depth filtration, wherein the depth filtration comprises a depth filter selected from the group consisting of a COHC depth filter, a XOHC depth filter, a synthetic hybrid depth filter (e.g., Emphaze™), or combinations thereof.

In some embodiments, the method further comprises analyzing at least one impurity. In a certain embodiment, the at least one product-related impurity is selected from the group consisting of a misfolded antibody, an aggregate, a truncation, a half-antibody, a modified antibody, and a peptide extension. In a certain embodiment, the at least one product-related impurity is a peptide extension comprising the amino acid sequence of SEQ ID NO: 1. In some embodiments, the method results in the antibody that is substantially free of at least one impurity. In some embodiments, the method results in the antibody obtained from the method of any of the methods described herein. In some embodiments, the antibody is selected from the group consisting of an anti-lysyl oxidase homolog 2 (LOXL2) antibody and an anti-metalloproteinase 9 (MMP9) antibody. In a certain embodiment, the antibody comprises the sequences set forth in SEQ ID NOs. 2 and 3, SEQ ID NOs. 4 and 5, SEQ ID NOs. 8 and 13, SEQ ID NOs. 14-19, SEQ ID NOs. 20 and 21, SEQ ID NOs. 20 and 23, SEQ ID NOs. 24-29, SEQ ID NO. 30, SEQ ID NO. 31, SEQ ID NOs. 32-34, SEQ ID NOs. 35 and 36, SEQ ID NOs. 37 and 38, SEQ ID NOs. 39-44, SEQ ID NOs. 45 and 46, SEQ ID NOs. 47 and 48, or SEQ ID NOs. 49 and 50. In some embodiments, the host cell culture fluid comprises at least one host cell protein. In a certain embodiment, the host cell protein is Phospholipase B-Like 2 (PLBL2).

DETAILED DESCRIPTION

Terms

The following description is presented to enable a person of ordinary skill in the art to make and use the various embodiments. Descriptions of specific methods, compositions, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but are to be accorded the scope consistent with the claims.

Unless defined otherwise, all technical and scientific terms used herein have the same meaning as is commonly understood by one of ordinary skill in the art to which this application belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference. The headings provided herein are for convenience only and do not limit the application in any way. All patents, applications, published applications and other publications referred to herein are incorporated by reference in their entirety.

As used in the present specification, the following words and phrases are generally intended to have the meanings as set forth below, except to the extent that the context in which they are used indicates otherwise. The term "about" includes and describes the value or parameter per se. For example, "about x" includes and describes "x" per se. In certain embodiments, the term "about" when used in association with a measurement, or used to modify a value, a unit, a constant, or a range of values, refers to variations of +/−1-10%. In some embodiments, the term "about" when used in association with a measurement, or used to modify a value, a unit, a constant, or a range of values, refers to variations of +/−5%. In some embodiments, the term "about" when used in association with a measurement, or used to modify a value, a unit, a constant, or a range of values, refers to variations of +/−10%. The term "between" includes and describes the value or parameter per se. For example, "between x and y" includes and describes "x" and "y" per se. The term "and/or" includes subject matter in the alternative as well as subject matter in combination. For instance, "x, and/or y", includes "x or y" and "x and y". Also, the singular forms "a", "an" and "the" include plural references unless the context clearly dictates otherwise. Thus, e.g., reference to "the antibody" includes a plurality of such antibodies and reference to "the assay" includes reference to one or more assays and equivalents thereof known to those skilled in the art.

It is understood that aspects and embodiments of the application described herein include "comprising," "consisting," and "consisting essentially of" aspects and embodiments.

The term "antibody" as used herein means any immunoglobulin, including monoclonal, bispecific, and polyclonal antibodies, including $IgG_1$, $IgG_{2a}$, $IgG_{2b}$, $IgG_4$ and others. The term is used herein as a collective noun that refers to a population of immunoglobulin molecules and/or immunologically active portions of immunoglobulin molecules, i.e., molecules that contain an antibody combining site or paratope. Thus, reference to an "antibody" also includes reference to any of the antigen binding fragments of antibodies. The antibodies may be from a wide variety of hosts and may be, for example, an engineered chimeric antibody or CDR-grafted antibody, including humanized antibodies. By way of example, antibody or antibodies may be derived from any mammalian species, including, but not limited to, humans, monkeys, pigs, horses, rabbits, dogs, cats, mice, etc., or other animals such as birds (e.g., chickens). Accordingly, the term "antibody" include but is not limited to immunoglobulin molecules isotype (e.g., IgG, IgE, IgM, IgD, IgA and IgY), immunoglobulin molecules subisotype (e.g., IgG1, IgG2, IgG3, IgG4, IgA1 and IgA2), immunoglobulin molecules allotype (e.g., Gm, e.g., G1 m(f, z, a or x), G2m(n), G3m(g, b, or c), Am, Em, and Km(1, 2 or 3)), monoclonal antibodies (including full-length monoclonal antibodies), polyclonal antibodies, multi specific antibodies formed from at least two different epitope binding fragments (e.g., bispecific antibodies), CDR-grafted, human antibodies, humanized antibodies, camelised antibodies, chimeric antibodies, anti-idiotypic (anti-Id) antibodies, intrabodies, antigen-binding fragments thereof, recombinantly produced antibody fragments, and the like. An antibody useful in the present application is understood to have affinity to protein A.

The term "mAb" refers to a monoclonal antibody. The term "half antibody" refers to one immunoglobulin heavy chain which is associated to one immunoglobulin light chain. One of skill in the art would also recognize that the term "half antibody" may refer to Fab or Fab' fragments.

The term "antibody fragments," "antigen-binding fragments," or variations thereof refer to antibody or the antigen-binding fragments which exhibits a desired biological activity. Antibody fragments may be produced by the methods that are commonly used in the art, such as recombinantly produced. By way of example, "antibody fragments," "antigen-binding fragments," or variation thereof include, but are not limited to, antibody fragments that include variable heavy- and light-chain domains, single-chain Fvs (scFv), single-chain antibodies, Fab fragments, Fab' fragments, $F(ab')_2$ fragments, epitope-binding fragments or derivatives of any of the antibodies described herein.

An "isolated antibody" includes an antibody that is substantially free of other antibodies having different antigenic specificities (e.g., an isolated antibody that specifically binds MMP-9 is substantially free of antibodies that specifically bind antigens other than MMP-9). Moreover, an isolated antibody may be substantially free of other cellular material and/or chemicals.

The term "target antibody," "target antigen-binding fragments," "desirable antibody," "desirable antigen-binding fragments," "purified antibody," "purified antigen-binding fragments," or variations thereof may refer to antibodies or antigen-binding fragments thereof which exhibit a desired biological activity and expressed by a host cell, followed by the methods of isolation, purification, or process according to the present disclosure. Accordingly, target antibodies or antigen-binding fragments thereof may be substantially free of other cellular materials, and/or impurities. As used herein, the target antibody may refer to any antibody that would be suitable to be used with the methods described herein. In one embodiment, the target antibody that is suitable for the method described herein is anti-MMP antibody (such as anti-MMP9 antibody), anti-LOX antibody, anti-LOXL antibody (including anti-LOXL2 antibody), or anti-DDR antibody (including anti-DDR2 antibody).

The term "antibody obtained from the method" or variations thereof refer to antibodies or antibody fragments purified, produced, processed, or isolated by any of the methods described herein. In some embodiments, the antibody or antibody fragment is a target antibody. In some embodiments, the antibody or antibody fragment is an isolated antibody.

The term "impurity," "product impurity," or variation thereof refers to undesirable chemical or biological materials, including biological macromolecules such as DNA, RNA, or a protein, other than a target antibody, antigen-binding fragment thereof, or antibody fragment that is present in a sample or a mixture or composition comprising a target antibody or antigen-binding fragment thereof. Without being bound to any theories, "impurity," "product impurities," or variation thereof may result from fragments that result from undesired disruption of one or more bonds along the peptide backbone of a desired antibody product (from non-enzymatic and/or enzymatic reactions), aggregates, or host cell proteins that are removed from the sample or a mixture such that the resulting antibody would provide therapeutic benefits without undesired adverse effects. In some embodiments, an impurity may be undesirable materials from HCCF. In certain embodiments, an impurity may be undesirable materials from HCP, such as phospholipase-B-like 2 protein (PLBL2). In certain embodiments, an impurity may be a target antibody that is modified by containing a peptide extension. The term "aggregates" used herein means agglomeration or oligomerization of two or more individual molecules, including but not limiting to, protein dimers, trimers, tetramers, oligomers and other high molecular weight species. The aggregates may be soluble or insoluble.

The term "fragments" used herein refers to any truncated protein species from the target molecule due to dissociation of peptide chain, enzymatic and/or chemical modifications.

The terms "host cell protein" (HCP), "host cell proteins" (HCPs) or variations thereof refer to non-target protein-related, proteinaous impurities derived from host cells. By way of example, HCP includes but is not limited to host phospholipase-B-like 2 protein (PLBL2).

The term "cell culture supernatant" refers to a solution that is obtained by culturing host cells that produce a recombinant antibody of interest or a target antibody. In addition to the recombinant antibody or target antibody, the cell culture supernatant may also include components of cell culture medium, metabolic byproducts secreted by the host cells as well as other components of the cultured cells. In some embodiments, cell culture supernatant may be a composition from which the host cells have been removed or harvested, such that the cell culture supernatant is generally free of cellular debris and/or intact cells. In certain embodiments, cell cultural supernatant is harvested using centrifuge and/or depth filtration to result in harvest cell culture fluid (HCCF). HCCF includes HCPs and a target antibody.

The phrase "host cell" or "host cells" refers to cells which express a recombinant polypeptide, for example, a recombinant antibody or recombinant antibody fragment. As used in the present disclosure, host cell can or has taken up a nucleic acid, such as a vector, and supports replication of the nucleic acid and production of one or more encoded products. Also, host cell refer to a variety of cell types including but not limited to prokaryotic cells, such as *Escherichia coli, Lactococcus lactis* and *Bacillus* species; eukaryotic cells, including yeast cells, such as *Pichia pastoris, Pichia methanolica*, and *Saccharomyces cerevisiae*, insect cell, such as bacuolovirus and eukaryotic cells; mammalian cells, such as Chinese hamster ovary (CHO) cells, human embryonic kidney (HEK 293) cells, Vero cells, baby hamster kidney (BHK) cells, HeLa cells, CV1 monkey kidney cells, Madin-Darby Canine Kidney (MDCK) cells, 3T3 cells, myeloma cell lines, COS cells (e.g., COS 1 and COS 7) PCl2, WI38 cells. In some instance, host cell may encompass combinations or mixtures of cells such as mixed cultures of different cell types or cell lines.

The term "purify" or "purifying" a target antibody or desired fragment thereof from a composition or solution that includes the target antibody or desired fragment thereof and one or more contaminants means increasing the degree of purity of the target antibody or desired antibody fragment thereof in the composition or solution by removing (completely or partially) at least one contaminant from the composition or solution. According the present application, the methods described herein would result in an antibody or an target antibody that is purified (i.e. purified antiboby) or substantially free of undesired moleules such as impurities, product impurities, aggregates, fragments, proteins, nucleic acids, cell culture supernatant, host cells, or host cell proteins. By way of example, the term "protein A purified antibody" referred to an antibody or a target antibody that is produced, purified, processed, or isolated by loading a mixture or a host cell culture fluid onto protein A chromatograph matrix. The protein A purified antibody may be further produced, purified, processed, or isolated by one or more steps or methods described herein to result in a final purified or isolated antibody. For example, the protein A purified antibody would be subject to one or more step of binding to depth filtration, membrane filtration, a cation exchange chromatography, a mixed-mode chromatography, ultrafiltration, diafiltration, or combination thereof, to result in a final purified antibody or final isolated antibody. The antibody purified, produced, processed, or isolated using the methods described herein may be used for any suitable purpose, including and not limited to characterization, testing, evaluation as well as in-vitro, in vivo, animal studies, pre-clinical studies, clinical studies, diagnostic, detection, therapeutics, or treatment. In some embodiments, the purified antibody or isolated antibody may be used or prepared for a pharmaceutically acceptable composition.

The terms "bind," "binding" or variations thereof when discussing the interaction between a molecule and a column material means exposing the molecule to the column material under conditions such that the molecule is reversibly immobilized in or on the column material.

The terms "remove," "removal" or variations thereof when used in context of removal of antibody fragmentation product impurities, refers to decrease in the amount of antibody fragmentation product impurities in the purified product. Removal may or may not result in the absence of impurities from the purified product. By way of example, removal refers to at least a 2 fold, 3 fold, 4 fold, 5 fold, 10 fold, 15 fold, 20 fold, 25 fold and up to 30 fold, 35 fold, 40 fold, 45 fold or 50 fold decrease in impurities in the purified product when compared to the level of impurities in the original composition.

The term "substantially pure" refers to a target material that is the predominant species present (e.g., on a molar basis it is more abundant than any other individual species in the composition). In one embodiment, a substantially purified fraction is a composition wherein the target material includes at least about 50% (on a molar basis) of all macromolecular species present. Generally, a substantially pure composition may include more than about 80% target molecule as compared to all macromolecular species present in the composition, or more than about 85%, more than about 90%, more than about 95%, more than about 96%, more than about 97%, more than about 98%, or more than about 99% target material. In one embodiment, the target material is purified to essential homogeneity (contaminant species cannot be detected in the composition by conventional detection methods) and the composition includes essentially a single macromolecular species, for example, the target macromolecule or target antibody.

The term "substantially free," "substantially free of" or variations thereof refers to a target material (such as a target antibody, purified antibody, or isolated antibody) having less than about 30%, less than about 25%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, or less than about 1% by weight, volume, or percentage of undesired molecules (such as impurities product impurities, aggregates, fragments, proteins, nucleic acids, cell culture supernatant, host cells, or host cell proteins). In one embodiment, "substantially pure" or "substantially free of" refers to a target material or an antibody preparation that is free of impurities. In certain embodiment, "substantial free" refers to a target material or an antibody preparation having about 20% or less of undesired molecules, about 19% or less of undesired molecules, about 18% or less of undesired molecules, about 17% or less of undesired molecules, about 16% or less of undesired molecules, about 15% or less of undesired molecules, about 14% or less of undesired molecules, about 13% or less of undesired molecules, about 12% or less of undesired molecules, about 11% or less of undesired molecules, about 10% or less of undesired molecules, about 9% or less of undesired molecules, about 8% or less of undesired molecules, about 7% or less of undesired molecules, about 6% or less of undesired molecules, about 5% or less of undesired molecules, about 4% or less of undesired molecules, about 3% or less of undesired molecules, about 2% or less of undesired molecules, or about 1% or less of undesired molecules.

The term "recombinant" refers to a biological material, for example, a nucleic acid or protein, that has been artificially or synthetically (i.e., non-naturally) altered or produced by human intervention.

The term "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242).

The term "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "polypeptide" or "protein" may be used interchangeably to refer to a molecule having two or more amino acid residues joined to each other by peptide bonds. The term "polypeptide" refers to antibodies and other non-antibody proteins. Non-antibody proteins include, but are not limited to, proteins such as enzymes, receptors, ligands of a cell surface protein, secreted proteins and fusion proteins or fragments thereof. The polypeptide may or may not be fused to another polypeptide. Polypeptides may also include modifications such as, but not limited to, glycosylation, lipid attachment, sulfation, gamma-carboxylation of glutamic acid residues, hydroxylation, and ADP-ribosylation. Polypeptides may be of scientific or commercial interest, including protein-based therapeutics.

The term "nucleic acid molecule" includes DNA molecules and RNA molecules. A nucleic acid molecule may be single-stranded or double-stranded, but in one aspect is double-stranded DNA. The phrase "isolated nucleic acid molecule" is also intended to include sequences encoding bivalent, bispecific antibodies, such as diabodies in which VH and VL regions contain no other sequences other than the sequences of the diabody.

The term "viral reduction/inactivation" refer to a decrease in the number of viral particles in a particular sample ("reduction"), as well as a decrease in the activity, for example, but not limited to, the infectivity or ability to replicate, of viral particles in a particular sample ("inactivation"). Such decreases in the number and/or activity of viral particles may be on the order of about 1% to about 99%, about 20% to about 99%, about 30% to about 99%, about 40% to about 99%, about 50% to about 99%, about 60% to about 99%, about 70% to about 99%, about 80% to 99%, and about 90% to about 99%. In certain non-limiting embodiments, the amount of virus, if any, in the purified antibody product is less than the $ID_{50}$ (the amount of virus that will infect 50 percent of a target population) for that virus, at least 10-fold less than the $ID_{50}$ for that virus, at least 100-fold less than the $ID_{50}$ for that virus, and at least 1000-fold less than the $ID_{50}$ for that virus.

The term "depth filtration" as used herein means filtering with a filtration device comprising diatomaceous earth. In some examples, depth filtration utilizes a porous filtration medium that retains particles throughout the porous filtration medium, such as by comprising diatomaceous earth. This depth filtration device may be a multi-layer filtration device composed of a series of stacked filters having gradually decreasing pore sizes and may have a three-dimensional maze-like structure. Examples of the mechanism of action of such a depth filtration device include, but are not limited to, a mechanism in which the device is cationic and thus binds anionic substances, such as DNA and host cell proteins. Alternatively, the device is anionic and thus binds cationic substances.

The term "membrane filtration" as used herein means generally a technique that uses a physical barrier, a porous membrane or filter, to separate particles in a fluid and or concentrate molecules in a fluid. Particles are separated on the basis of their size and shape with the use of pressure and specially designed membranes with different pore sizes. Membrane filtration methods include, reverse osmosis, nanofiltration, ultrafiltration and microfiltration, in order of increasing pore size.

The term "ultrafiltration" as used herein refers to the process of separating impurities by passing a composition through one or more semi-permeable filter(s) (or membrane or medium) of a specified pore size diameter, wherein larger molecular weight molecules (e.g., >100 Da) are retained on the filter and lower molecular weight molecules pass through the filter. The lower molecular weight molecules may be media components, antibody fragments, and/or other impurities (contaminants) such as lipopolysaccharides.

The term "diafiltration" as used herein refers to the use of ultrafiltration membranes to completely remove, replace, or lower the concentration of salts or solvents from solutions containing proteins, peptides, nucleic acids, and other biomolecules.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and/or decreased viscosity. Examples of excipients include, but are not limited to, proteins (for example, but not limited to, serum albumin), amino acids (for example, but not limited to, aspartic acid, glutamic acid, lysine, arginine, glycine), surfactants (for example, but not limited to, SDS, Tween 20, Tween 80, polysorbate and nonionic surfactants), saccharides (for example, but not limited to, glucose, sucrose, maltose and trehalose), polyols (for example, but not limited to, mannitol and sorbitol), fatty acids and phospholipids (for example, but not limited to, alkyl sulfonates and caprylate).

The term "pharmaceutically acceptable" as used herein means approved by a regulatory agency of a Federal or state government, or listed in the U.S. Pharmacopeia, European Pharmacopia or other generally recognized pharmacopeia for use in animals, and more particularly in humans.

The term "stability," "stable" or variations thereof when used in the context of a formulation of a recombinantly produced polypeptide, for example, a pharmaceutical formulation that includes a recombinantly produced antibody or antibody fragment, refer to the resistance of the polypeptide in the formulation to particle formation, aggregation, degradation or fragmentation under manufacture, preparation, transportation and storage conditions. A "stable" formulation retains biological activity under manufacture, preparation, transportation and storage conditions. Stability may be assessed by degrees of particle formation, aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, as compared to a reference formulation.

Antibodies obtained from a variety of sources usually contain impurities derived from the host and/or cell culture matrix. The methods for the purification of antibodies according to the application provide for the removal of one or more undesired impurities. In certain aspects, the methods provide for the removal of host cell protein (HCP), for example, phospholipase-B-like 2 protein (PLBL2). In an embodiment, the methods of the application are suitable for removing impurities from HCCF, such as, for example, PLBL2.

In certain embodiments, the methods of the present application result in antibody recoveries from HCCF of at least 60%. In certain embodiments, the methods of the present application result in antibody recoveries from HCCF of at least 65%. In certain embodiments, the methods of the present application result in antibody recoveries from HCCF of at least 70%. In embodiments, the antibody recovery is from about 70% to about 100%, from about 80% to about 100%, or from about 85% to about 95%. In another embodiment, the antibody recovery is at least 90%, 91%, 92%, 93%, 94%, 95%, 96%, 97%, 98%, 99% or 100% and any range there between. In certain embodiments, the methods of the present application result in a purified antibody preparation having a reduction in HCP content as compared to HCCF of from about 500 fold to about 50,000 fold, from about 1,000 fold to about 40,000 fold, from about 10,0000 fold to about 30,0000 fold. In an embodiment, the methods of the application result in a purified antibody preparation having a reduction in HCP levels as compared to HCCF of 500 fold, 1,000 fold, 10,000 fold, 20,000 fold, 30,000 fold, 40,000 fold, or 50,000 fold, and any range there between. In certain embodiments, the methods of the present application result in a purified antibody preparation having a reduction in PLBL2 content as compared to HCCF of about 50 fold to about 10,000 fold. In an embodiment, the reduction in PLBL2 content is from about 100 fold to about 1000 fold. In an embodiment, the reduction in PLBL2 content in the purified antibody as compared to HCCF is about 300 fold.

In certain embodiments, the methods of the present application result in target antibody recoveries from HCCF of at least 60%, at least 65%, at least 70%, at least 75%, at least 80%, at least 85%, or at least 90%, at least 95%, at least 96%, at least 97%, at least 98%, or at least 99%. In some embodiments, the target antibody recovery is from about 70% to about 100%, from about 80% to about 100%, or from about 85% to about 95%. In another embodiment, the target antibody recovery is at least 90%, 91%, 92%, 93%, 94%, 95%, 96%, 97%, 98%, 99% or 100% and any range there between. In certain other embodiments, the methods of the present application result in a purified target antibody preparation having a reduction in HCP content as compared to HCCF of from about 500 fold to about 50,000 fold, from about 1,000 fold to about 40,000 fold, from about 10,0000 fold to about 30,0000 fold. In an embodiment, the methods of the application result in a purified target antibody preparation having a reduction in HCP levels as compared to HCCF of 500 fold, 1,000 fold, 10,000 fold, 20,000 fold, 30,000 fold, 40,000 fold, or 50,000 fold, and any range there between. In certain embodiments, the methods of the present application result in a purified target antibody preparation having a reduction in PLBL2 content as compared to HCCF of about 50 fold to about 10,000 fold. In an embodiment, the reduction in PLBL2 content is from about 100 fold to about 1000 fold. In an embodiment, the reduction in PLBL2 content in the purified target antibody as compared to HCCF is about 300 fold.

Antibodies

The antibodies of the present disclosure may be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody may be employed e.g., viral or oncogenic transformation of B lymphocytes. In one embodiment, the animal system for preparing hybridomas is the murine system.

Hybridoma production is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure may be prepared based on the sequence of a non-human monoclonal antibody prepared as described herein. DNA encoding the heavy and light chain immunoglobulins may be obtained from the non-human hybridoma of interest and engineered to contain non-murine (e.g., human) immunoglobulin sequences using standard molecular biology techniques. For example, to create a chimeric antibody, murine variable regions may be linked to human constant regions using methods known in the art (see, e.g., U.S. Pat. No. 4,816,567). To create a humanized antibody, murine CDR regions may be inserted into a human framework using methods known in the art (see, e.g., U.S. Pat. Nos. 5,225,539; 5,530,101; 5,585,089; 5,693,762; and 6,180,370). Any recombinantly expressed, cultured, or otherwise generated antibody may be purified using the methods described herein. In certain embodiments, antibodies suitable for use with the methods described herein are anti-LOXL2 antibodies, anti-MMP9 antibodies, anti-DDR1 antibodies, and anti-DDR2 antibodies.

Antibodies may be purified using the methods described herein include and are not limited to anti-MMP antibodies (including anti-MMP9 antibodies), anti-LOX antibodies, anti-LOXL2 antibodies (anti-LOXL2 antibodies), and anti-DDR antibodies (including anti-DDR1 antibodies). Examples of anti-MMP9 antibodies include and are not limited to those disclosed in U.S. 2015-0140580, U.S. Pat. Nos. 8,377,443; 8,501,916; 9,120,863; and 9,260,532, the disclosures of which are incorporated herein by reference in their entirety. In a certain embodiment, the anti-MMP9 antibody comprises a heavy chain polypeptide comprising the amino acid sequence selected from the group consisting of SEQ ID NOs: 2, 20, 36, and 45. In a certain embodiment, the anti-MMP9 antibody comprises a light chain polypeptide comprising the amino acid sequence selected from the group consisting of SEQ ID NOs: 3, 21, 30, 35, and 46. In a certain embodiment, the anti-MMP9 antibody comprises a heavy chain polypeptide comprising a variable region comprising the amino acid sequence selected from the group consisting of SEQ ID NOs: 4, 6-9, 22, and 37. In a certain embodiment, the anti-MMP9 antibody comprises a light chain polypeptide comprising a variable region comprising the amino acid sequence selected from the group consisting of SEQ ID NOs: 5, 10-13, 23, 31, and 38. In a certain embodiment, the anti-MMP9 antibody comprises a heavy chain polypeptide comprising complementarity-determining regions (CDRs) with the amino acid sequences of SEQ ID NOs: 14-16. In a certain embodiment, the anti-MMP9 antibody comprises a light chain polypeptide comprising complementarity-determining regions (CDRs) with the amino acid sequences of SEQ ID NOs: 17-19. In a certain embodiment, the anti-MMP9 antibody comprises a heavy chain polypeptide comprising complementarity-determining regions (CDRs) with the amino acid sequences of SEQ ID NOs: 24-26. In a certain embodiment, the anti-MMP9 antibody comprises a light chain polypeptide comprising complementarity-determining regions (CDRs) with the amino acid sequences of SEQ ID NOs: 27-29. In a certain embodiment, the anti-MMP9 antibody comprises a light chain polypeptide comprising complementarity-determining regions (CDRs) with the amino acid sequences of SEQ ID NOs: 32-34. In a certain embodiment, the anti-MMP9 antibody comprises a heavy chain polypeptide comprising complementarity-determining regions (CDRs) with the amino acid sequences of SEQ ID NOs: 39-41. In a certain embodiment, the anti-MMP9 antibody comprises a light chain polypeptide comprising complementarity-determining regions (CDRs) with the amino acid sequences of SEQ ID NOs: 42-44. In a certain embodiment, the anti-MMP9 antibody comprises a heavy chain polypeptide comprising the amino acid sequence of SEQ ID NO: 2, and a light chain polypeptide comprising the amino acid sequence of SEQ ID NO: 3, and may be referred to as AB0041. In a certain embodiment, the anti-MMP9 antibody comprises a heavy chain polypeptide comprising a variable region comprising the amino acid sequence of SEQ ID NO: 4, and a light chain polypeptide comprising a variable region comprising the amino acid sequence of SEQ ID NO: 5, and may be referred to as AB0041. In a certain embodiment, the anti-MMP9 antibody comprises a heavy chain polypeptide comprising the amino acid sequence of SEQ ID NO: 36, and a light chain polypeptide comprising the amino acid sequence of SEQ ID NO: 35, and may be referred to as AB0046. In a certain embodiment, the anti-MMP9 antibody comprises a heavy chain polypeptide comprising a variable region comprising the amino acid sequence of SEQ ID NO: 37, and a light chain polypeptide comprising a variable region comprising the amino acid sequence of SEQ ID NO: 38, and may be referred to as AB0046. In a certain embodiment, the anti-MMP9 antibody comprises a heavy chain polypeptide comprising complementarity-determining regions (CDRs) with the amino acid sequences of SEQ ID NOs: 39-41, and a light chain polypeptide comprising complementarity-determining regions (CDRs) with the amino acid sequences of SEQ ID NOs: 42-44. In a certain embodiment, the anti-MMP9 antibody comprises a heavy chain polypeptide comprising the amino acid sequence of SEQ ID NO: 45, and a light chain polypeptide comprising the amino acid sequence of SEQ ID NO: 46. In a certain embodiment, the anti-MMP9 antibody comprises a heavy chain polypeptide comprising a variable region comprising the amino acid sequence of SEQ ID NO: 8, and a light chain polypeptide comprising a variable region comprising the amino acid sequence of SEQ ID NO: 13. In a certain embodiment, the anti-MMP9 antibody comprises a heavy chain polypeptide comprising complementarity-determining regions (CDRs) with the amino acid sequences of SEQ ID NOs: 14-16, and a light chain polypeptide comprising complementarity-determining regions (CDRs) with the amino acid sequences of SEQ ID NOs: 17-19. In one embodiment, the anti-MMP9 antibody has the CDRs of a heavy chain polypeptide comprising a variable region comprising the amino acid sequence of SEQ ID NO: 8, and the CDRs of a light chain polypeptide comprising a variable region comprising the amino acid sequence of SEQ ID NO: 13. In a certain embodiment, the methods described herein may be used to produce, process, purify, or isolate an anti-MMP9 antibody AB0045 from a mixture or a host cell culture.

Examples of anti-LOX antibodies and anti-LOXL2 antibodies include and are not limited to those described in WO 2009/035791 and US 2009/0053324, the disclosures of which is incorporated herein by reference in their entirety. In a certain embodiment, the anti-LOXL2 antibody comprises a heavy chain polypeptide comprising a variable region comprising the amino acid sequence selected from the group consisting of SEQ ID NOs: 47 and 49. In a certain embodiment, the anti-LOXL2 antibody comprises a light chain polypeptide comprising a variable region comprising the amino acid sequence selected from the group consisting of SEQ ID NOs: 48 and 50. In a certain embodiment, the anti-LOXL2 antibody comprises a heavy chain polypeptide comprising a variable region comprising the amino acid sequence of SEQ ID NO: 47, and a light chain polypeptide comprising a variable region comprising the amino acid sequence of SEQ ID NO: 48, and may be referred to as AB0023. In a certain embodiment, the anti-LOXL2 antibody comprises a heavy chain polypeptide comprising a variable region comprising the amino acid sequence of SEQ ID NO: 49, and a light chain polypeptide comprising a variable region comprising the amino acid sequence of SEQ ID NO: 50, and may be referred to as AB0024. In one embodiment, the anti-LOXL2 antibody has the CDRs of a heavy chain polypeptide comprising a variable region comprising the amino acid sequence of SEQ ID NO: 49, and the CDRs of a light chain polypeptide comprising a variable region comprising the amino acid sequence of SEQ ID NO: 50, and may be referred to as AB0024. In a certain embodiment, the methods described herein may be used to produce, process, purify, or isolate an anti-LOXL2 antibody AB0024 from a mixture or a host cell culture. The methods described herein may be suitable to purify, process, produce, or isolate the antibody comprising the sequence selected from the group consisting of SEQ ID NOs: 2, 3, 4, 5, 8, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or combination thereof.

Antibody Production

Prior to the process or method of the present application, initial procedures for purification of antibodies from cell debris may be performed, depending on the site or location of expression of the antibody. Some antibodies may be secreted directly from the cell into the surrounding growth media; others are made intracellularly. For the latter antibodies, the first step of a purification process typically involves: lysis of the cell, which may be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells may also be separated from the cell culture medium, e.g., by tangential flow filtration. Antibodies may be further recovered from the culture medium using the antibody purification methods described herein.

The present application provides a method for producing a purified (or "HCP-reduced" or "impurity-reduced") antibody preparation from a mixture comprising an antibody and at least one HCP or impurity. The purification process described herein begins at the separation step when the antibody has been produced using methods described above and conventional methods in the art. The purification scheme may comprise the steps of harvest, depth filtration, protein A chromatography, viral inactivation, pH adjustment, cation exchange chromatography, mixed mode chromatography, viral filtration, and/or ultrafiltration/diafiltration. Variations of this scheme, including, but not limited to, variations where cation exchange chromatography is omitted, mixed mode chromatography is omitted, and/or the order of the fine purification steps is reversed, are envisaged and are within the scope of the presentation. In some embodiments, the purification scheme comprises the steps of harvest (using centrifuge and/or depth filtration), protein A chromatography (including loading/absorbing/capturing target antibody from a mixture such as HCCF with protein A matrix, which is followed by one or more wash solution), viral inactivation (using low pH, such as a pH of about 3.4 to about 3.8, for 30-90 minutes for inactivation), pH adjustment (adjusting to a pH of about 5.0 to about 7.5, such as a pH of 6.0, depth filtration COHc→XOHC), cation exchange chromatography (using a cation exchange matrix, such as Poros XS), mixed mode chromatography (using a mixed-mode matrix, such as Capto adhere), viral filtration (for removing remaining viruses), and ultrafiltration diafiltration (for concentrate and formulate proteins).

Once a clarified solution or mixture comprising the antibody (i.e., the harvest cell culture fluid (HCCF)) has been obtained, separation of the antibody from the other proteins produced by the cell, such as HCPs, is performed using a combination of different purification techniques, including protein A chromatography, ion exchange separation step(s), and hydrophobic interaction separation step(s). The separation steps separate mixtures of proteins on the basis of their charge, degree of hydrophobicity, or size, or a combination thereof. Separation may be performed using chromatography, including protein A resin, and cationic, anionic, and hydrophobic interaction. Several different chromatography resins may be employed to control or modify the purification scheme to the particular protein involved, such as the target antibody. Various proteins may migrate at different rates down a column, achieving a physical separation that increases as they pass further down the column, or to adhere selectively to the separation medium, being then differentially eluted by different solvents. In some cases, the antibody is separated from impurities when the impurities specifically adhere to the column and the antibody does not, i.e., the antibody is present in the flow through. Other factors may include, but are not limited to: the presence or absence of an Fc region (e.g., in the context of full length antibody as compared to an Fab fragment thereof) because Protein A binds to the Fc region; the particular germline sequences employed in generating to antibody of interest; the amino acid composition of the antibody (e.g., the primary sequence of the antibody as well as the overall charge/hydrophobicity of the molecule); and the presence of a modification to the antibody, such as a peptide extension. Antibodies sharing one or more characteristic may be purified using purification strategies tailored to take advantage of that characteristic.

The methods described herein would be useful for processing, isolating, or purifying any antibodies. Antibodies may be generated in cell culture, in phage, or in various animals, including but not limited to cows, rabbits, goats, mice, rats, hamsters, guinea pigs, sheep, dogs, cats, monkeys, chimpanzees, and apes. An antibody useful in the present methods may be from any species but is typically a mammalian antibody. In one embodiment, the antibody is produced by recombinant means known in the art. For example, a recombinant antibody may be produced by transfecting a host cell with a vector comprising a DNA sequence encoding the antibody. One or more vectors may be used to transfect the DNA sequence expressing at least one variable light (VL) region and one variable heavy (VH) region in the host cell. Exemplary descriptions of recombinant means of antibody generation and production include Delves, Antibody Production: Essential Techniques (Wiley, 1997); Shephard, et al., Monoclonal Antibodies (Oxford University Press, 2000); and Goding, Monoclonal Antibodies: Principles and Practice (Academic Press, 1993). Also, antibodies may be made according to the protocol described by in Kenney, et al. ("Production of monoclonal antibodies using a secretion capture report web." Biotechnology 13:787-790, 1995). Briefly, mice are injected subcutaneously (s.c.), with antigen in an adjuvant formulation. For peptide antigens, peptides are conjugated to bovine serum albumin and formulated in Freund's Adjuvant (FA) prior to immunization. For protein antigens, the protein is formulated in Alhydrogel-Muramyl Dipeptide (ALD/MDP) adjuvant. Cells from the spleen and lymph nodes of the mice are isolated and fused with appropriate cells and cultured. A hybridoma library of hypoxantine-aminopterin-thymidine (HAT)-selected cells is isolated and is cloned. Cells are sorted and sera and supernatants are screened for the presence of antibodies.

For high level production, the most widely used mammalian expression system is one which utilizes the gene amplification procedure offered by dihydrofolate reductase ("dhfr-") or GS (glutamine synthetase) expression system in Chinese Hamster ovary (CHO) cells. The system is well known to the skilled artisan. The system is based upon the dihydrofolate reductase "dhfr" gene, which encodes the DHFR enzyme, which catalyzes conversion of dihydrofolate to tetrahydrofolate. Another well-known example of a selection system utilized for cell line generation is the glutamine synthetase (GS) expression system. GS is a dominant selectable marker that can be used with GS-negative and wildtype cells, such as CHO cells that contain an active endogenous GS gene. GS selection requires either the use of the GS enzyme inhibitor methionine sulfoximine (MSX) or the use of an engineered cell line which lacks functional GS enzyme activity in combination with glutamine free selection. In order to achieve high production, CHO cells are transfected with an expression vector containing a functional dhfr or GS gene, together with a gene that encodes a desired protein. In this case, the desired protein is recombinant antibody heavy chain and/or light chain.

In addition, the expression of antibodies and antibody fragments in prokaryotic cells such as *Escherichia coli* (*E. coli*) is well established in the art (Pluckthun, A. Bio/Technology 9:545-551 (1991). Expression in eukaryotic cells in culture is available to those skilled in the art as an option for production of the antibodies and antigen-binding fragments (Raff, M. E. (1993) Curr. Opinion Biotech. 4:573-576; Trill J. J. et al. (1995) Curr. Opinion Biotech 6:553-

560). In one embodiment, the target antibody is an anti-lysyl oxidase homolog 2 (LOXL2) antibody, and functional fragments thereof, which may be generated according to methods well known in the art. Exemplary anti-LOXL2 antibodies, including AB0023 and AB0024, are described in WO 2009/035791 and US 2009/0053324. In another embodiment, the antibody is an anti-metalloproteinase 9 (MMP9) antibody, and functional fragments thereof, which may be generated according to methods well known in the art. Exemplary anti-MMP9 antibodies and fragments thereof, including AB0041 and AB0045, are disclosed in U.S. 2015-0140580, U.S. Pat. Nos. 8,377,443; 8,501,916; 9,120,863; and 9,260,532.

Following in vitro culture of antibody-producing cells, the cell culture fluid is harvested, thereby providing HCCF. The HCCF is then subject to purification according to the methods of the present disclosure. Antibody obtained from other sources may also be purified in accordance with the methods disclosed herein.

Chromatography

An embodiment of the application employs an immobilized protein A matrix as a protein A affinity step in purifying antibodies. Suitable protein A affinity matrix include but not limited to MabSelect SuRe™, MabSelect SuRe PCC™, MabSelect SuRe LX™ (GE Healthcare Life Sciences, Marlborough, Mass.), Amsphere Protein ATM resin (JSR Life Sciences), and ProSep® Ultra Plus (EMD Millipore Corporation, Billerica, Mass.). In some instance, the dynamic binding capacity (DBC) of the Protein A resin would be determined for the antibody of interest. For example, the DBC of a MabSelect™ column may be determined either by a single flow rate load or dual-flow load strategy. The single flow rate load may be evaluated at a velocity of about 300 cm/hr throughout the entire loading period. The dual-flow rate load strategy may be determined by loading the column up to about 35 mg protein/mL resin at a linear velocity of about 300 cm/hr, then reducing the linear velocity by half to allow longer residence time for the last portion of the load. The immobilized protein A matrix may be in the form of a column or may be used as a slurry in batch purification. Suitable columns for packing with MabSelect™ SuRe include a 1.0 cm×21.6 cm column (about 17 mL bed volume) which may be suitable for small scale purifications or a 20 cm×21 cm column (about 6.6 L bed volume) which may be suitable for large scale purifications. Whether employed in column or batch format, protein A affinity chromatography methodologies are known in the art. As used herein, the term "chromatrophy," "matrix," or "chromatography matrix" are interchangeable.

In some embodiments, a protein L matrix is used as an alternative to the protein A matrix, and, in some embodiments, is used in accordance with one or more of the methodologies described herein with respect to protein A chromatography, as well as those methodologies for protein L chromatography known in the art. In one embodiment, the protein L matrix is Capto L (GE Healthcare Life Sciences, Marlborough, Mass.).

In one embodiment, the protein A matrix is MabSelect SuRe™, hereinafter referred to as MSS. Protein A matrix may be equilibrated with a suitable solution prior to sample (such as HCCF) loading. After equilibration, protein A matrix may be optionally washed one or multiple times using equilibrating solution or different solution prior to sample loading. After desirable time to allow a target antibody to absorb to protein A matrix, one or more wash solutions would be employed to remove HCPs. Subsequently, the target antibody which is purified with protein A matrix (i.e. protein A purified antibody) would be eluted using an appropriate eluting solution. In certain embodiments, the equilibrating solution comprises 25 mM Tris, 25 mM NaCl, and is at pH of about 7.7. In some embodiments, the eluting solution comprises 40 mM acetic acid and is at pH of about 3.1. In other embodiments, the protein A matrix is equilibrated with the equilibrating solution before and after sample loading.

The elution may be monitored using techniques well known to those skilled in the art. For example, the absorbance at 280 nm may be used, and the eluate may be collected starting with an initial deflection of about 0.5 AU to a reading of about 0.5 AU at the trailing edge of the elution peak. The elution fraction(s) of interest may then be prepared for further processing or purification. For example, the collected sample (or primary recovery) may be titrated to a lower pH, then filtered using depth filtration, and then subject to further separation steps (such as additional chromatography steps).

The terms "equilibration buffer," "equilibrating solution," or variations thereof refer to a buffer that may be used to remove undesired residual from the matrix before or after loading the target protein, by adjusting the pH of the column. For example, an equilibration buffer may be applied to the protein A matrix as part of the protein A chromatography step. When used for antibody purification, the pH of the equilibration buffer is at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. The equilibration buffer may be based on tris(hydroxymethyl)aminomethane ("Tris") (pH range 5.8-8.0), 4-(2-hydroxyethyl)-1-piperazineethanesulfonic acid (HEPES) (pH range 6.8-8.2), 3-(N-morpholino)propanesulfonic acid (MOPS) (pH range 6.5-7.9) or other phosphate buffering agents (pH 5.8-8.0).

The terms "elution buffer," "eluting solution," or variations thereof refer to a buffer that may be used to elute (i.e., remove or collect) the target from the matrix. The elution pH may vary depending upon the binding affinity of the protein or antibody to the matrix. Typically, the elution buffer for a protein A matrix has a pH of at least about 2.0, 2.1, 2.2, 2.3, 2.4, 2.5, 2.6, 2.7, 2.8, 2.9, 3.0, 3.1, 3.2, 3.3, 3.4, or 3.5 and up to about 3.6, 3.7, 3.8, 3.9, 4.0, 4.1, 4.2, 4.3, 4.4, 4.5, 4.7, 4.8, 4.9 or 5.0. The elution buffer for use with a mixed-mode matrix typically has a pH of at least about 4.5, 4.6, 4.7, 4.8, 4.9, or 5.0, and up to about 5.1, 5.2, 5.3, 5.4, 5.5, 5.6, 5.7, 5.8, 5.9, or 6.0. Examples of elution buffers include buffers comprising sodium citrate, citric acid, or acetic acid. Some elution buffers also include one or more of calcium chloride, sodium chloride, ammonium acetate, and ammonium chloride.

Any of the solutions described herein may further include one or more agents that would increase protein purity, stability, and function. Examples include, but are not limited to reducing agents such as 2-mercaptoethanol (BME), dithiothreiotol (DDT) or Tris(2-carboxyethyl)phosphine (TCEP) to protect against oxidative damage, protease inhibitors, including but not limited to leupeptin, pepstatin A and phenylmethanesulfonylfluoride (PMSF) to inhibit endogenous proteases from degrading the target polypeptide, metal chelators, including but not limited to ethylenediaminetetraacetic acid (EDTA) and ethylene glycol tetra-acetic acid (EGTA), to inactivate metalloproteases, osmolytes, including but not limited to glycerol, detergents and sugars to stabilize protein structure or ionic stabilizers, including but not limited to salts such as NaCl, KCl and $(NH_4)_2SO_4$ to enhance solubility.

According to the application, the target antibody to be purified, isolated, or processed is harvested from cell culture in a HCCF prior to capturing the antibody on the protein A matrix. Methodologies for harvesting antibodies, for example in HCCF or any other source, are known in the art. In an embodiment, the cell culture may be a mammalian cell culture, such as a Chinese hamster ovarian (CHO) cell culture and the harvesting may employ continuous centrifugation and/or depth filtration. Accordingly to the present application, the HCCF may be depth filtered with any suitable depth filter. In one embodiment, an XOHC depth filter (EMD Millipore Corporation, Billerica Mass.) may be used. In one embodiment, a synthetic hybrid depth filter, e.g., Emphaze™ filter (3M™ Emphaze™ AEX Hybrid Purifier) may be used for depth filtration.

The harvested antibody is adsorbed onto the protein A matrix by any means known in the art. In an embodiment, the protein A matrix may be in the form of a column and the HCCF may be loaded onto the column by conventional means. In an embodiment, the protein A chromatography may be performed in batch mode in which the harvested antibody is incubated with a protein A matrix and the antibody is permitted to adsorb over time to the protein A. In another embodiment, harvested antibody is added to protein A matrix in a resin slurry or a packed bed or column. The flow rates (if column format is used) and/or incubation times (if batch format is used) for the adsorption step may be modified to increase the amount of antibody adsorbed onto the protein A matrix.

After a sufficient time that allows the antibody to be adsorbed or loaded onto the protein A matrix, the protein A matrix is washed with at least one wash solution comprising one or more additives. By way of example, the one or more additives is selected from urea, arginine, guanidine, caprylate, and sodium chloride. In an embodiment, at least one additive is urea. In an embodiment, at least one additive is arginine. In an embodiment, at least one additive is guanidine. In an embodiment, at least one additive is caprylate. In an embodiment, at least one additive is sodium chloride. In an embodiment, at least one additive is sodium phosphate. In an embodiment, the wash solution comprises urea and sodium chloride. In an embodiment, the wash solution comprises caprylate and sodium chloride. The wash solution comprising urea may also be referred to as "urea wash solution" or "urea solution" which is used interchangeably herein. It is understood that similar terms may be used for a wash solution comprising one or more other additives.

In the present application, the wash solution may be at a pH from 5.0 to 9.5. In some embodiments, the wash solution has a pH value of less than about 9.0, less than about 8.5, less than 8.0, less than 7.5, less than 7.0, less than 6.5, less than 6.0, less than 5.5, or less than 5.0. In some other embodiments, the wash solution is at a pH more than 5.0 and less than about 9.0, less than about 8.5, less than 8.0, less than 7.5, less than 7.0, less than 6.5, less than 6.0, or less than 5.5. In some other embodiments, the wash solution is at a pH more than 5.5 and less than about 9.0, less than about 8.5, less than 8.0, less than 7.5, less than 7.0, less than 6.5, or less than 6.0. In certain other embodiments, the wash solution is at a pH more than 6.0 and less than about 9.0, less than about 8.5, less than 8.0, less than 7.5, less than 7.0, or less than 6.5. In other embodiments, the wash solution is at a pH more than 6.5 and less than about 9.0, less than about 8.5, less than 8.0, less than 7.5, or less than 7.0. In some other embodiments, the wash solution is at a pH more than 7.0 and less than about 9.0, less than about 8.5, less than 8.0, or less than 7.5. In one other embodiment, the wash solution is at a pH more than 7.5 and less than about 9.0, less than about 8.5, or less than 8.0. In yet another embodiment, the wash solution is at a pH more than 8.0 and less than about 9.0 or less than about 8.5. In certain embodiments, the wash solution is at a pH value of 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, or 9.5. In other embodiments, the wash solution is at a pH between 5.0 to 5.5, between 5.5 to 6.0, between 6.0 to 6.5, between 6.5 to 7.0, between 7.0 to 7.5, between 7.5 to 8.0, between 8.0 to 8.5, between 8.5 to 9.0, between 9.0 to 9.5, between 5.0 to 6.0, between 5.0 to 6.5, between 5.0 to 7.0, between 5.0 to 7.5, between 5.0 to 8.0, between 5.0 to 8.5, between 5.0 to 9.0, between 5.0 to 9.5, between 5.5 to 6.5, between 5.5 to 7.0, between 5.5 to 7.5, between 5.5 to 8.0, between 5.5 to 8.5, between 5.5 to 9.0, between 5.5 to 9.5, between 6.0 to 7.0, between 6.0 to 7.5, between 6.0 to 8.0, between 6.0 to 8.5, between 6.0 to 9.0, between 6.0 to 9.5, between 6.5 to 7.5, between 6.5 to 8.0, between 6.5 to 8.5, between 6.5 to 9.0, between 6.5 to 9.5, between 7.0 to 8.0, between 7.0 to 8.5, between 7.0 to 9.0, between 7.0 to 9.5, between 7.5 to 8.5, between 7.5 to 9.0, between 8.0 to 9.0, or between 8.0 to 9.5. Any suitable buffer may be used to achieve the desired pH of the wash solution. By way of example, the buffer is sodium phosphate, Tris (2-Amino-2-(hydroxymethyl)-1,3-propanediol or tris(hydroxymethyl)aminomethane). In one embodiment, the buffer is sodium phosphate. In another embodiment, the buffer is Tris (2-Amino-2-(hydroxymethyl)-1,3-propanediol or tris(hydroxymethyl)aminomethane).

The method of present application comprises a washing step, comprising the use of at least one urea wash solution. The urea wash solution or the urea solution comprises from about 4000 mM (4 M) to about 8000 mM (8 M) urea. In certain embodiments, the urea wash solution comprises urea at about 4000 mM (4 M), about 4500 mM (4.5 M), about 5000 mM (5 M), about 5500 mM (5.5 M), about 6000 mM (6 M), about 6500 mM (6.5 M), about 7000 mM (7 M), about 7500 mM (7.5 M), or about 8000 (8 M). Moreover, the urea wash solution may be at a pH from about 5.0 to about 8.5. In one embodiment, the urea wash solution is at a pH less than about 9.0. In other embodiments, the urea wash solution is at a pH less than about 8.5. In one embodiment, the urea wash solution is pH 5.5. In an embodiment, the urea wash solution is pH 5.8. In another embodiment, the urea wash solution is pH 6.5. In another embodiment, the urea wash solution is pH 7.7. In yet another embodiment, the urea wash solution is pH 8.2. In some other embodiments, the urea wash solution is pH 8.5. The urea wash solution may comprise up to 1500 mM (1.5 M) sodium chloride (NaCl). In an embodiment, the urea wash solution comprises 500 mM (0.5 M) to 1000 mM (1 M) NaCl. In another embodiment, the urea wash solution comprises 0 mM (0 M) NaCl. In an embodiment, the urea wash solution comprises 4000 mM urea, 1000 mM NaCl, and is at a pH of about 7.7. In another embodiment, the urea wash solution comprises 6000 mM urea, 1500 mM NaCl, and is at a pH of about 7.7. In another embodiment, the urea wash solution comprises 6000 mM Urea, 0 mM NaCl, and is at a pH of about 8.2. In yet another embodiment, the urea wash solution comprises 6000 mM urea, 1500 mM NaCl, and is at a pH of about 8.2.

After antibody loading, at least one wash of the protein A matrix is performed with the urea wash solution. In one embodiment, at least two washes are performed with the urea wash solution. In a further embodiment, at least three washes are performed with the urea wash solution. In an embodiment, additional washes may be performed with a wash solution that does not comprise urea as an additive, such as the arginine wash solution, the guanidine wash solution, the NaCl wash solution, or the caprylate wash solution. The flow rates (if column format is used) and/or incubation times (if batch format is used) for the wash step (including where there are multiple washes) may be modified to control or modulate the amount of HCP reduction and/or antibody recovery. In an embodiment, the flow rate of the wash step is from about 50 cm/hr to about 400 cm/hr. In another embodiment, the flow rate is from about 75 cm/hr to about 250 cm/hr. In a further embodiment, the flow rate of the wash step using a urea wash solution is from about 75 cm/hr to about 150 cm/hr. In a certain embodiment, the flow rate of the wash step using a urea wash solution is 100 cm/hr.

In some aspect, the method of present application comprises a washing step, comprising at least one wash solution comprising arginine as an additive, which solution may be referred to as the arginine wash solution or the arginine solution. In an embodiment, the washing step comprising the arginine wash solution comprises at least one wash with the arginine wash solution in addition to at least one wash with the urea wash solution. The arginine wash solution may comprise from about 100 mM (0.1 M) to about 1000 mM (1 M) arginine. For example, the arginine wash solution may comprise about 100 mM (0.1 M), about 200 mM (0.2 M), about 300 mM (0.3 M), about 400 mM (0.4 M), about 500 mM (0.5 M), about 600 mM (0.6 M), about 700 mM (0.7 M), about 800 mM (0.8 M), about 900 mM (0.9 M), or about 1000 mM (1 M) arginine. In an embodiment, the arginine wash solution comprises from about 400 mM (0.4 M) to about 800 mM (0.8 M) arginine. In some embodiments, the arginine wash solution comprises about 100 mM, 400 mM, or 800 mM arginine. In certain embodiments, the arginine wash solution comprises about 800 mM arginine. Also, the arginine wash solution may be at a pH of from about 5.0 to about 8.0. For example, the arginine wash solution may be at a pH of about 5.8, about 6.5, or about 7.7. In a further embodiment, the arginine wash solution comprises 800 mM arginine and is at a pH of about 7.7.

In certain aspect, the method of present application comprises a washing step, comprising at least one wash solution comprising guanidine as an additive, which solution may be referred to as the guanidine wash solution or the guanidine solution. In an embodiment, the washing step comprising the use of the guanidine wash solution comprises at least one wash with the guanidine wash solution in addition to at least one wash with the urea wash solution. In one embodiment, the guanidine wash solution comprises from about 500 mM (0.5 M) guanidine to about 1000 mM (1 M) guanidine. For example, the guanidine wash solution may comprise about 500 mM (0.5 M), about 600 mM (0.6 M), about 700 mM (0.7 M), about 800 mM (0.8 M), about 900 mM (0.9 M), or about 1000 mM (1 M) guanidine. In certain embodiments, the guanidine wash solution may comprise about 600 mM or about 1000 mM guanidine. Also, the guanidine wash solution may be at a pH of from about 5.0 to about 8.0. For example, the guanidine wash solution may be at a pH of about 5.8, about 6.5, or about 7.7. In some embodiments, the guanidine wash solution comprises 1000 mM guanidine and is at a pH of about 7.7.

In other aspect, the method of present application comprises a washing step, comprising at least one wash solution comprising sodium chloride (NaCl) as an additive, which solution may be referred to as the NaCl wash solution or the NaCl solution. In an embodiment, the washing step comprising the use of the NaCl wash solution comprises at least one wash with the NaCl wash solution in addition to at least one wash with the urea wash solution. In some embodiments, the NaCl wash solution may comprise 500 mM (0.5 M) to 1000 mM (1 M) of NaCl. For example, the NaCl wash solution may comprise about 500 mM (0.5 M), about 600 mM (0.6 M), about 700 mM (0.7 M), about 800 mM (0.8 M), about 900 mM (0.9 M), or about 1000 mM (1 M) NaCl. In certain embodiments, the NaCl wash solution may comprise about 500 mM or about 1000 mM NaCl. The NaCl wash solution may be at a pH of about 5.0 to about 8.0. For example, the NaCl wash solution may be at a pH of about 5.8, about 6.5, or about 7.7. In an embodiment, the NaCl wash solution comprises 500 mM NaCl and is at a pH of about 7.7.

In certain aspect, the method of present application comprises a washing step, comprising at least one wash solution comprising caprylate as an additive, which solution may be referred to as the caprylate wash solution or the caprylate solution. In an embodiment, the washing step comprising the use of the caprylate wash solution comprises at least one wash with the caprylate wash solution in addition to at least one wash with the urea wash solution. In one embodiment, the caprylate wash solution comprises from about 1 mM caprylate to about 50 mM caprylate. For example, the caprylate wash solution may comprise about 1 mM, about 5 mM, about 10 mM, about 15 mM, about 20 mM, about 25 mM, about 30 mM, about 35 mM, about 40 mM, about 45 mM, about 50 mM caprylate. In certain embodiments, the caprylate wash solution may comprise about 5 mM or about 25 mM caprylate. Also, the caprylate wash solution may be at a pH of from about 5.0 to about 8.0. For example, the caprylate wash solution may be at a pH of about 5.8, about 6.5, or about 7.7. In additional embodiments, the caprylate wash solution comprises 25 mM caprylate and is at a pH of about 7.7.

In an embodiment, the method of the present application comprises a washing step, comprising at least one wash solution comprising glycine as an additive, which solution may be referred to as the glycine wash solution or the glycine solution. In an embodiment, the washing step comprising the use of the glycine wash solution comprises at least one wash with the glycine wash solution in addition to at least one wash with the urea wash solution. In one embodiment, the glycine wash solution comprises from about 100 mM (0.1 M) to about 1000 mM (1 M) glycine. For example, the glycine wash solution may comprise about 100 mM, about 100 mM, about 300 mM, about 400 mM, about 500 mM, about 600 mM, about 700 mM, about 800 mM, about 900 mM, or about 1000 mM glycine. In some embodiments, the glycine wash solution comprises from about 500 mM (0.5 mM) to about 1000 mM (1 M) NaCl. For example, the glycine wash solution may comprise about 500 mM, about 600 mM, about 700 mM, about 800 mM, about 900 mM or about 1000 mM NaCl. In some embodiments, the glycine wash solution may be at a pH of from about 5.0 to about 8.5, such as a pH of about 8.0. In some embodiments, the glycine wash solution comprises 300 mM glycine and 500 mM NaCl and is at a pH of 8.0.

According to the present application, in an embodiment, at least one wash solution comprises at least two additives, wherein one additive is sodium chloride at a concentration from about 500 mM (0.5 M) to 1000 mM (1 M) of NaCl, or from about 500 mM (0.5 M) to about 1500 mM (1.5 M) of NaCl. Such wash solution may comprise NaCl at about 500 mM (0.5 M), about 600 mM (0.6 M), about 700 mM (0.7 M), about 800 mM (0.8 M), about 900 mM (0.9 M), about 1000 mM (1 M), about 1100 mM (1.1 M), about 1200 mM (1.2 M), about 1300 mM (1.3 M), about 1400 mM (1.4 M), or about 1500 mM (1.5 M). In certain embodiments, the wash solution comprises at least two additives, wherein one additive is sodium chloride at about 500 mM or about 1000 mM or about 1500 mM. In certain embodiments, the wash solution comprising at least two additives comprises sodium chloride as one additive and urea as a second additive.

At least one wash of the protein A matrix is performed with the wash solution of any of the embodiments described herein. In an embodiment, at least two washes are performed. In a further embodiment, at least three washes are performed. It is understood that the flow rates and/or incubation times for the wash step may be modified to control the amount of HCP reduction and/or antibody recovery. The wash step may include one wash solution, wherein the column is washed using at least about 5, or up to about 10 or 20 column volumes of a single wash solution. Also, the process may include more than one wash solution, for example, the process may include two different wash solutions. For example, the process may include a urea wash solution as one wash solution and an arginine wash solution, guanidine wash solution, NaCl wash solution, or caprylate wash solution as an additional wash solution.

Any of the foregoing wash solutions and wash flow rates may be combined and used to achieve any desired recovery levels of target antibody and sufficient reduction of HCP, or impurities such as PLBL2, from HCCF.

After the protein A matrix is washed with at least one wash solution, the antibody is eluted from the protein A matrix to obtain a protein A purified antibody. Any suitable buffer known in the art may be used to elute the antibody from the protein A matrix. The eluting buffer or eluting solution comprises from about 5 mM to about 65 mM acetic acid. Also, the eluting solution is at a pH of from about 2.5 to 3.5. In one embodiment, the eluting solution comprises 5 mM to about 65 mM acetic acid and at a pH of about 2.7 to 3.4. In some embodiments, the eluting solution comprises 5 mM to about 65 mM acetic acid and at a pH of about 2.9 to 3.4. In other embodiments, the eluting buffer comprises 40 mM acetic acid and is at a pH of 3.1. The flow rate and/or incubation time for the elution step may be modified to control the amount of antibody recovery. In an embodiment, the flow rate of the elution step is from about 50 cm/hr to about 400 cm/hr. In another embodiment, the flow rate of the elution step is from about 75 cm/hr to about 300 cm/hr. In a further embodiment, the flow rate of the elution step is from about 75 cm/hr to about 150 cm/hr. In another embodiment, the flow rate of the elution step is from about 250 cm/hr to about 300 cm/hr. In certain embodiments, the flow rate of the elution step is 100 cm/hr. In some embodiments, the flow rate of the elution step is 265 cm/hr. In one embodiment, the protein A matrix is equilibrated with the solution comprising 25 mM Tris, 25 mM NaCl, and is at pH of about 7.7. In one embodiment, after sample loading, the protein A matrix (i.e. the loaded protein A matrix) is washed with the equilibrating solution, followed by the urea wash solution and the equilibrating solution, wherein the equilibrating solution comprises 25 mM Tris, 25 mM NaCl, and is at pH of about 7.7. Any of the foregoing solutions and flow rates may be combined and used for any desired recovery levels of the target antibody and sufficient reduction of HCP content, or impurities such as PLBL2, from HCCF.

The method described herein would provide a purified target antibody that may be sufficient for therapeutic applications using only one chromatography step, e.g., protein A affinity chromatography. Additional steps, including but not limited to chromatography, viral inactivation, and/or filtration, may be optionally employed in accordance with the present application. Additional chromatography steps are known in the field.

Viral Inactivation and Depth Filtration

In an embodiment, the protein A purified antibody may be subject to viral inactivation by any means known in the art. When referring to the inactivation of viruses, the virus particles may remain in the final product but in a non-infective form. The virus inactivation step may comprise a pH inactivation step and/or a chemical inactivation step.

The pH inactivation step may include adjusting the pH to inactivate the virus. In an embodiment, the protein A purified antibody may be incubated at low pH to inactivate viral impurities. In one embodiment, the protein A purified antibody is incubated at a pH below 4.0, for example, from about 3.4 to about 3.8. The protein A purified antibody may be adjusted to a pH of less than 4.0 by the addition of acid, for example acetic acid, to achieve the desired pH. In an embodiment, the protein A purified antibody is adjusted to a pH of about 3.4 to about 3.8, for example, with acetic acid. To inactivate viral impurities, the pH adjusted protein A purified antibody is incubated for at least 30 minutes to inactivate virus. In one embodiment, the viral inactivation incubation time is about 60 minutes. In another embodiment, the viral inactivation incubation time is about 90 minutes.

After incubating at a pH of less than 4.0, the pH of the protein A purified antibody may be adjusted to a pH of about 4.0 to about 9.0. In some embodiments, the pH is adjusted to 5.0. In certain embodiments, the pH is adjusted to 6.0. Any suitable buffer may be used to adjust the pH. In one embodiment, tris base may be used to adjust the pH. In an embodiment, the pH is adjusted to a pH of about 5.5 to about 6.5, or to a pH of about 5.8 to about 6.0. Additional HCP may precipitate from the protein A purified antibody after the pH is increased after viral inactivation. In an embodiment, the precipitated HCP may be removed by depth filtration. In other embodiments, at least one depth filtration step is employed on the viral inactivated, pH adjusted protein A purified antibody. In another embodiment, at least two depth filtration steps are employed on the viral inactivated, pH adjusted protein A purified antibody. Any depth filtration means known in the art may be used. In an embodiment, the depth filtration means is selected from the group consisting of COHC and XOHC (both available from EMD Millipore Corporation, Billerica, Mass.), and combinations thereof. In an embodiment, COHC depth filtration is performed on the viral inactivated, pH adjusted protein A purified sample and, thereafter, XOHC depth filtration is performed. In another embodiment, the depth filtration means is selected from the group consisting of COHC (EMD Millipore Corporation, Billerica, Mass.) and a synthetic hybrid depth filter, e.g., Emphaze™ (3M™ Emphaze™ AEX Hybrid Purifier). In an embodiment, COHC depth filtration is performed on the viral inactivated, pH adjusted protein A purified sample and, thereafter, depth filtration using a synthetic hybrid depth filter, e.g., Emphaze™, is performed. According to the present application, by using a depth filter(s), the HCP content is reduced, and, for example, the percent reduction of HCP is about 45% to about 85%.

In an embodiment, the method includes a membrane filtration step. The membrane filtration step may be employed before or after viral inactivation and/or depth filtration. Membrane filtration is well known in the art and suitable membrane filtration devices will be readily apparent to the skilled artisan. It may be desired to chemically inactivate virus in the antibody preparation. The chemical inactivation step may include treatment with solvents or detergents, irradiation, and/or brief exposures to high temperatures sufficient to inactivate a virus. These methods of viral inactivation as known to those skilled in the art, and one of skill in the art may select an appropriate treatment condition.

Mixed-Mode Chromatography

In an embodiment, the protein A purified antibody may be subject to a mixed-mode chromatography step. The mixed-mode chromatography step may be performed after the protein A purification step, and/or after the viral inactivation step and/or after the depth filtration step, and/or after the cation exchange chromatography step. In an embodiment, the mixed-mode chromatography step is performed after the cation exchange chromatography step. In an embodiment, the mixed-mode chromatography step is performed after the protein A chromatography step. The mixed-mode chromatography step may be performed in a bind and elute manner and/or a flow through mode. For example, it may be useful to employ a mixed-mode chromatography step in a bind and elute manner in which the antibody binds to the mixed-mode chromatography matrix while impurities do not bind. After binding of the antibody to the mixed-mode matrix, the antibody is eluted to obtain a purified antibody. Alternatively, it may be useful to employ a mixed-mode chromatography step in a flow through manner in which the antibody does not bind (flows through) but impurities bind to the mixed-mode chromatography matrix. The skilled person in the field may adapt the conditions to obtain either binding or flow-through of the antibodies, e.g., by adjustment of pH, conductivity, or addition of different chaotropic and kosmotropic salts to optimize the hydrophobic interactions, which will depend, for example, on the charge and charge distribution of the antibodies to be purified or on combination of electrostatic (local surface charge) and hydrophobic patches on the target antibody and impurities.

The mixed-mode chromatography matrix used in the present disclosure is, for example, a chromatography matrix consisting of a carrier with a multimodal ligand immobilized thereon, the ligand comprising one or more anion or cation exchange groups and one or more aromatic or heterocyclic aromatic systems. Exemplary mixed-mode cation exchange matrices having hydrophobic or hydrogen bonding capabilities include, but are not limited to, Capto MMC and Capto MMC ImpRes, available from GE Healthcare Life Sciences (Marlborough, Mass.). Exemplary mixed-mode anion exchange matrices having hydrophobic or hydrogen bonding capabilities include, but are not limited to, Capto Adhere and Capto Adhere ImpRes, available from GE Healthcare Life Sciences (Marlborough, Mass.).

In one embodiment, the mixed-mode chromatography step comprises an anion exchange mixed-mode matrix that is employed in a bind and elute manner. The mixed-mode chromatography step is useful to remove HCP, such as PLBL2, as well as any Protein A leachate from the protein A purification step. The mixed-mode chromatography step is also useful in removing product related impurities with different sequences (e.g. fragments, elongated species or Fc modified species). In one embodiment, the mixed mode chromatography is capable of removing a peptide sequence extension of an antibody with a mass difference of, for example, +1177 Da. Conditions for the mixed-mode chromatography step that are known in the art may be employed. One or more washing steps may also be employed, particularly if the bind and elute manner is utilized. In an embodiment, an anion exchange mixed-mode matrix, e.g., Capto Adhere or Capto Adhere ImpRes (GE Healthcare Life Sciences, Marlborough, Mass.), is used in a bind and elute manner. In a certain embodiment the protein A purified antibody is bound to the mixed-mode matrix at a pH of from about 7.0 to about 9.0, from about 7.5 to about 8.5. The binding buffer may include Tris. The binding buffer may also include from about 35 mM to about 65 mM NaCl, from about 40 mM to about 55 mM NaCl. Once loaded onto the mixed-mode matrix, in an embodiment, the antibody may be eluted from the mixed-mode matrix at a pH of from about 4.5 to about 6.0, from about 5.0 to about 5.6. The elution buffer may include from about 90 mM to about 150 mM calcium chloride ($CaCl_2$), from about 95 to about 110 $CaCl_2$. In one embodiment, the elution buffer may include from about 120 to about 200 mM NaCl, from about 150 to about 180 mM NaCl. In another embodiment, the elution buffer may include from about 80 mM to about 175 mM ammonium acetate ($NH_4OAc$). In another embodiment, the elution buffer may include 32 mM ammonium chloride ($NH_4Cl$).

Additional Chromatography Steps

Additional chromatography steps may be employed in the present disclosure. Examples include anion exchange (AEX), cation exchange (CEX), hydrophobic interaction (HIC), hydrophilic interaction, hydrogen bonding, pi-pi bonding, metal affinity, and affinity chromatography (including protein G, chromatographic material comprising the antigen bound by the antibody of interest, and chromatographic material comprising an Fc binding protein) or any combination thereof. For example, anion exchange or cation exchange chromatography may be employed before or after the mixed-mode step. Anion and cation exchange chromatography matrices are well known in the art. Examples of cation exchange matrices include Capto™ S and SP Sepharose FF® (GE Healthcare Life Sciences, Marlborough, Mass.), as well as S Ceramic HyperD™ and HyperCel™ Star CEX (PALL Corporation, Port Washington, N.Y.), and Poros® XS. Examples of anion exchange matrices that may be utilized include Capto Q and Capto DEAE (GE Healthcare Life Sciences, Marlborough, Mass.), as well as Q Ceramic HyperD™ and HyperCel™ Star AX (PALL Corporation, Port Washington, N.Y.).

Hydrophobic interaction chromatography, based on hydrophobic interaction separation, may remove protein aggregates, such as antibody aggregates, and process-related impurities. Hydrophobic interaction chromatography steps may be performed simultaneously with ion exchange chromatography steps with chromatography resin having both ion exchange functions and hydrophobic functions. Such resins are characterized as mixed mode chromatography resins. In performing the separation, the sample mixture is contacted with the HIC material, e.g., using a batch purification technique or using a column. Prior to HIC purification it may be desirable to remove any chaotropic agents or very hydrophobic substances, e.g., by passing the mixture through a pre-column. Adsorption of the antibody to a HIC column is favored by high salt concentrations, but the actual concentrations may vary over a wide range depending on the nature of the antibody and the particular HIC ligand chosen. Various ions may be arranged depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++}$; $Ca^{++}$; $Mg^{++}$; $Li^+$; $Cs^+$; $Na^+$; $K^+$; $Rb^+$; $NH_4^+$, while anions may be ranked in terms of increasing chaotropic effect as $PO—$; $SO_4—$; $CH_3CO_3—$; $Cl—$; $Br—$; $NO_3—$; $ClO_4—$; $I—$; $SCN—$. HIC columns normally comprise a base matrix (e.g., cross-linked agarose or synthetic copolymer material) to which hydrophobic ligands (e.g., alkyl or aryl groups) are coupled. A suitable HIC column comprises an agarose resin substituted with phenyl groups (e.g., a Phenyl Sepharose™ column). Many HIC columns are available commercially. Examples include, but are not limited to, Phenyl Sepharose™ 6 Fast Flow column with low or high substitution; Phenyl Sepharose™ High Performance column; Octyl Sepharose™ High Performance column; Fractogel™ EMD Propyl or Fractogel™ EMD Phenyl columns; Macro-Prep™ Methyl or Macro-Prep™ t-Butyl Supports; WP HI-Propyl (C3)™ column; and Toyopearl™ ether, phenyl or butyl columns. Hydrophobic interaction resins that feature cationic functions are available commercially and include, but are not limited to, Capto MMC™, Capto MMC™ ImpRes (GE Healthcare, UK), Nuvia™ cPrime™ (Biorad, Calif.). Hydrophobic interaction resins (and membrane products) that feature anionic functions are available commercially and include, but are not limited to, QyuSpeed D (QSD) membrane and Sartobind Q membrane.

Filtration Steps

After the antibody is purified, the purified antibody may be subjected to filtration steps, including buffer exchange, that may be useful to remove viral particles and/or small molecules from the purified antibody, and/or to concentrate the purified antibody to a desired concentration. For virus removal by filtration, nanofiltration devices may be used. In an embodiment, the nanofiltration device may have a membrane that has a pore size of less than 75 nm, less than 50 nm, or less than 15 nm. In one embodiment, the method comprises a viral filtration step to provide a virus filtered purified antibody. For filtration to remove viral particles, any known filters may be used that are suitable for such removal. Exemplary devices for viral filtration include, but are not limited to, Viresolve® Pro Chromasorb™, Planova™, Plavnova™, and BioEx.

In an embodiment, the method comprises an ultrafiltration/diafiltration (UF/DF) step. UF/DF may be employed with or without a viral removal step to provide a concentrated antibody in the desired buffer. UF/DF is a combined operation of ultrafiltration and diafiltration. In an embodiment, the UF/DF step removes particles, concentrates the antibody, and exchanges/modified the aqueous or buffer composition of the purified antibody. Ultrafiltration and diafiltration are well known in the art. In some embodiments, filters, such as membrane ultrafilters, plate ultrafilters, cartridge ultrafilters, bag ultrafilters, or vacuum ultrafilters are employed. In some embodiments, 30 kD Pellicon® 3 membrane is employed from EMD Millipore Corporation. Commercially available UF/DF devices that may be employed are manufactured by various vendors, such as EMD Millipore Corporation, PALL Corporation, GE Healthcare Life Sciences, and Sartorious Corporation. Exemplary devices for UF/DF include, but are not limited to, Pellicon 3. According to the present application, each step (i.e. loading, washing, elution, filtration, or viral inactivation) may be repeated multiple times to achieve the desired purpose (i.e. purifying, processing, producing, or isolating an antibody) and each solution (i.e. washing solution, urea washing solution, elution solution/buffer) may be used multiple times. For example, each of the steps of loading, washing, elution, filtration, or viral inactivation may be repeated at least one, two, three, or four times.

The present application also provides methods for determining the residual levels of host cell protein (HCP) or target antibody in the isolated/purified antibody composition. As described above, HCPs are desirably excluded from the final target substance product; failure to identify and sufficiently remove HCPs from the target antibody may lead to reduced efficacy and/or adverse subject reactions. HCPs or target antibody may be characterized using commonly-used methods such as enzyme linked immunosorbent assay (ELISA), size-exclusion chromatography (SEC), for example, high performance size exclusion chromatography (HPSEC), sodium dodecyl sulfate-polyacrylamide gel electrophoresis (SDS-PAGE) and capillary electrophoresis with SDS (CE-SDS) and reverse phase high performance liquid chromatography (RP-HPLC).

EXAMPLES

The following nonlimiting examples relate to exemplary embodiments for antibody purification processes capable of reducing host cell proteins, including PLBL2, such that a purified antibody or target antibody preparation is provided. It is understood that the conditions (such as the reagent concentration, recovery values, incubation temperature, etc.) of the assay or study may be varied and the results of the assay or study may vary. In some instances, the value may vary within a range of at least one to two-fold.

Example 1

An anti-LOXL2 antibody and an anti-MMP9 antibody were produced in Chinese hamster ovary (CHO) cells under standard cell culture conditions. Examples of antibodies include an anti-LOXL2 antibody comprising a heavy chain polypeptide comprising the variable region of SEQ ID NO: 49, and a light chain polypeptide comprising the variable region of SEQ ID NO: 50. Examples of antibodies also include an anti-MMP9 antibody comprising the heavy chain polypeptide of SEQ ID NO: 45 and the light chain polypeptide of SEQ ID NO: 46. The host cell culture fluid (HCCF) comprising the antibodies was collected for further processing. The purification methods were tested for host cell protein (HCP). A cell line specific ELISA assay was employed for this analysis. Phospholipase B-Like2 (PLBL-2) was quantified by LC/MS. Samples were processed by proteolytic (trypsin) digests following denaturation, reduction, and alkylation. PLBL-2 in the test sample was converted to tryptic peptides. A PLBL-2 peptide, LTFPTGR, correlating to amino acids 159 to 165 in the mature Chinese hamster PLBL-2 sequence (Uniprot accession G3I6T1_CRIGR) was detected by a reverse-phase LC/HR-MRM method on an LTQ-Orbitrap mass spectrometer. The peptide was quantified using standardization of the signal in a test sample against a standard curve generated by spiking chemically synthesized peptide at different levels into a control sample (standard addition). Mass of the peptide in the test sample was numerically converted to moles of peptide, which indicated equivalent moles of intact PLBL-2 protein in the samples. The molar value of intact or whole PLBL-2 was converted to mass of the PLBL-2 for a weight/weight ratio comparison with the antibody (mass intact PLBL-2/mass anti-MMP9 antibody) and expressed in ppm. Protein concentration was standardized between test samples and quantitation standards prior to sample processing. The chromatography, mobile phases, and m/z isolations, was transferred for use on a tandem quadrupole mass spectrometer.

The HCCF comprising an anti-MMP9 antibody was loaded onto a protein A MSS matrix. The HCCF had an antibody titer of 2.55 g/L. Various wash solutions were tested for their ability to remove host cell proteins from the final purified antibody eluted from the column, as compared to control. Antibody that was eluted from the MSS matrix was adjusted with 2 M Acetic acid and neutralized with 2 M Tris Base to approximately pH 5.0 to 6.0 and then evaluated for protein recovery and HCP content.

The control wash solution was a standard protein A affinity chromatography solution and included 25 mM Tris and 500 mM NaCl (pH 7.7). The wash solutions tested in these experiments contained from 500 mM NaCl to 1500 mM NaCl, and/or from 500 mM urea to 6000 mM urea. Also, the pH range of the wash solutions tested in these experiments ranged from 5.8 to 8.2. Exemplary results are provided in Table 1 and described below.

TABLE 1

| Components | | pH | Recovery (%) | HCP (ppm) | HCP (Fold change) |
|---|---|---|---|---|---|
| HCCF | | | | 67115 | n/a |
| 1.5M NaCl | 25 mM Tris + 6M Urea | 7.7 | 98.1 | 262 | 256 |
| HCCF | — | — | — | 83490 | n/a |
| 0M NaCl | 25 mM Tris + 6M Urea | 7.7 | 97.7 | 83 | 1005 |
| 1.5M NaCl | 25 mM Tris + 6M Urea | 8.2 | 93.4 | 175.0 | 477 |

In another set of experiments, the initial or starting level of HCP in the HCCF MSS load starting material was measured to be about 43,300 ppm for this set of experiments. This was reduced to 519 ppm when the wash solution containing 0.5 M NaCl and 25 mM Tris (pH7.7); to 553 ppm when the wash solution containing 0.5 M NaCl and 25 mM sodium phosphate (pH 7.7); to 350 ppm (pH5.8) or 384 ppm (pH 7.7) when the wash solution containing 1.0 M NaCl, 1.0 M urea, and 25 mM sodium phosphate; to 241 ppm (pH 5.8) or 271 ppm (pH 7.7) when the wash solution containing 1.0 M NaCl, 2.0 M urea, and 25 mM sodium phosphate; to 96 ppm (pH 5.8) or 130 ppm (pH 7.7) when the wash solution containing 1.0 M NaCl, 4.0 M urea, and 25 mM sodium phosphate; to 273 ppm (pH 5.8) or 305 ppm (pH 7.7) when the wash solution containing 0.8 M arginine and 25 mM sodium phosphate; to 424 ppm (pH 5.8) or 413 ppm (pH 7.7) when the wash solution containing 0.6 M guanidine and 25 mM sodium phosphate; to 495 ppm when the wash solution containing 0.5 M NaCl, 25 mM caprylate, and 25 mM sodium phosphate (pH 7.7); and 655 ppm when the wash solution containing 0.01% Tween 20 and 25 mM sodium phosphate (pH 6.5).

The levels of antibody recovery at various washing conditions were also determined. The average level of antibody recovery was 97.4% when the wash solution containing 0.5 M NaCl and 25 mM Tris (pH7.7); 90.1% (pH 5.8), 99.2% (pH 6.5), or 100.4% (pH 7.7) when the wash solution containing 0.5 M NaCl and 25 mM sodium phosphate; 102.1% (pH 5.8), 105.5% (pH 6.5), or 101.6% (pH 7.7) when the wash solution containing 1.0 M NaCl and 25 mM sodium phosphate; 100.6% (pH 5.8), 99.1% (pH 6.5), or 104.3% (pH 7.7) when the wash solution containing 0.5 M NaCl, 0.5 M urea, and 25 mM sodium phosphate; 100.8% (pH 5.8), 103.8% (pH 6.5), or 103.8% (pH 7.7) when the wash solution containing 0.5 M NaCl, 1.0 M urea, and 25 mM sodium phosphate; 94.7% (pH 5.8), 98.6% (pH 6.5), or 99.4% (pH 7.7) when the wash solution containing 0.5 M NaCl, 2.0 M urea, and 25 mM sodium phosphate; 84.0% (pH 5.8), 91.4% (pH 6.5), or 94.4% (pH 7.7) when the wash solution containing 0.5 M NaCl, 4.0 M urea, and 25 mM sodium phosphate; 95.6% (pH 5.8), 101.9% (pH 6.5), or 101.8% (pH 7.7) when the wash solution containing 1.0 M NaCl, 0.5 M urea, and 25 mM sodium phosphate; 98.4% (pH 5.8), 105.9% (pH 6.5), or 101.8% (pH 7.7) when the wash solution containing 1.0 M NaCl, 1.0 M urea, and 25 mM sodium phosphate; 92.0% (pH 5.8), 98.1% (pH 6.5), or 97.6% (pH 7.7) when the wash solution containing 1.0 M NaCl, 2.0 M urea, and 25 mM sodium phosphate; 77.5% (pH 5.8), 90.2% (pH 6.5), or 93.8% (pH 7.7) when the wash solution containing 1.0 M NaCl, 4.0 M urea, and 25 mM sodium phosphate; 93.8% (pH 5.8), 102.7% (pH 6.5), or 101.0% (pH 7.7) when the wash solution containing 0.1 M arginine and 25 mM sodium phosphate; 102.1% (pH 5.8), 102.2% (pH 6.5), or 101.7% (pH 7.7) when the wash solution containing 0.4 M arginine and 25 mM sodium phosphate; 97.4% (pH 5.8), 99.9% (pH 6.5), or 99.1% (pH 7.7) when the wash solution containing 0.8 M arginine and 25 mM sodium phosphate; 98.9% (pH 5.8), 101.3% (pH 6.5), or 98.6% (pH 7.7) when the wash solution containing 0.6 M guanidine and 25 mM sodium phosphate; 99.3% (pH 5.8), 102.0% (pH 6.5), or 100.9% (pH 7.7) when the wash solution containing 1.0 M guanidine and 25 mM sodium phosphate; 93.2% (pH 5.0) or 104.3% (pH 7.7) when the wash solution containing 0.5 M NaCl, 10 mM caprylate, and 25 mM sodium phosphate; 100.6% (pH 6.5) or 101.9% (pH 7.7) when the wash solution containing 0.5 M NaCl, 25 mM caprylate, and 25 mM sodium phosphate (pH 7.7); and 100.9% (pH 5.8), 100.6% (pH 6.5), or 100.4% (pH 7.7) when the wash solution containing 0.01% Tween 20 and 25 mM sodium phosphate.

Results from this study indicate that wash solutions comprising arginine, guanidine, or a combination of urea with sodium chloride, resulted in a reduction of the HCP content in the range of pH 5.8 to pH 8.2 when tested as compared to the control. Selected elution pools were also evaluated for host cell protein PLBL2 levels using Mass Spectroscopy. The level of PLBL2 in the MSS load pool HCCF was about 1600 ppm. The HCP fold reduction with 4M Urea, 0.5 M NaCl compared to the control wash 0.5 M NaCl, pH 7.7, was changed from 78 fold to 338 fold. Results are provided in Table 2.

TABLE 2

| Wash Matrix | Intermediate | Overall HCP (ppm) | PLBL2 (Specific) LCMS | PLBL2 fold Reduction | HCP fold Reduction |
|---|---|---|---|---|---|
| | HCCF | 43299 | 1626 | N/A | N/A |
| 0.5M NaCl pH 7.7 (Control) | MabSelect SuRe Pool | 553 | 226 | 7 | 78 |
| 0.8M Arginine pH 7.7 | | 305 | 134 | 12 | 142 |
| 4M Urea, 1M NaCl pH 7.7 | | 128 | 31 | 53 | 338 |

In another set of experiments, HCCF comprising an anti-LOXL2 antibody was loaded onto protein A matrix. Various wash solutions were tested for their ability to facilitate the removal of host cell proteins from the final purified antibody eluted from the column (native pool), native pool after pH adjustment to pH 5.0-5.1 (pH 5 before filtration), and after pH adjustment and sterile filtration (pH adjusted pool/pH 5 EDF sterile) as compared to the same pools generated with a control wash solution.

The various wash conditions included a control wash solution (25 mM Tris, 500 mM NaCl (pH 7.7)); control wash solution further comprising 10 mM sodium citrate; urea wash solution comprising 2 M urea, 0.5 M NaCl, pH 7.7;

urea wash solution comprising 2 M urea, 0.5 M NaCl, pH 5.5; urea wash solution comprising 4M urea, 1 M NaCl, pH 7.7; glycine wash solution comprising 0.3 M glycine, 0.6 M NaCl, pH 8.0; and glycine wash solution comprising 0.3 M glycine, 0.6 M NaCl, 0.5% P80, pH 8.0. The levels of HCP in native, pH 5 before filtration, and pH adjusted/pH 5 EDF sterile filtered pools were measured and results summarized in Table 3.

The downstream process for the anti-MMP9 product using anion-exchange chromatography (such as Capto Q) consists of an affinity Protein A chromatography step, viral inactivation, depth filtration, cation-exchange chromatography, and anion-exchange chromatography. However, during the development of a modified process for the reduction of Hamster Phospholipase B-Like 2 (PLBL2) host cell protein, the final chromatography step (polishing step) was changed

TABLE 3

| Wash buffer | Native | Native Cond. (mS/cm) | Adj. pH | Adj. Cond. (mS/cm) | Pool Vol. (mL) | Pool CV | Conc. (g/L) | Yield (%) | % of Control | Native Pool HCP* (ng/mg) | pH Adj. Pool HCP* (ng/mg) |
|---|---|---|---|---|---|---|---|---|---|---|---|
| Control | 4.29 | 1.56 | 5.0 | 5.71 | 26.54 | 1.7 | 16.66 | 88 | 100 | 2599 | 949 |
| Control with 10 mM NaCitrate Elution | 4.42 | 0.88 | 5.1 | 4.05 | 31.69 | 2.0 | 14.1 | 89 | 101 | 1952 | 770 |
| 2M Urea; 0.5M NaCl pH 7.7 | 4.29 | 1.44 | 5.0 | 5.51 | 23.32 | 1.5 | 18.65 | 87 | 99 | 1280 | 778 |
| 2M Urea; 0.5M NaCl pH 5.5 | 4.32 | 1.26 | 5.0 | 5.82 | 21.15 | 1.3 | 19.4 | 82 | 93 | 736 | 442 |
| 4M Urea; 1M NaCl pH 7.7 | 4.32 | 1.42 | 5.0 | 5.75 | 21.43 | 1.4 | 19.8 | 85 | 97 | 902 | 610 |
| 0.3M Glycine, 0.6M NaCl pH 8 | 4.34 | 1.67 | 5.1 | 5.95 | 25.66 | 1.6 | 17.5 | 89 | 101 | 3418 | 1136 |
| 0.3M Glycine, 0.6M NaCl 0.5% P80 pH 8 | 4.29 | 1.58 | 5.1 | 5.45 | 27.23 | 1.7 | 16.12 | 87 | 99 | 3508 | 957 |

The hydrophobic index of IgG4 antibodies, including the anti-MMP9 antibody, the anti-LOXL2 IgG4 antibody, and a reference IgG4 antibody, was calculated using the Grand Average of Hydropathy (GRAVY) method. See, e.g., Kyte, J. and Doolittle, R. F., A simple method for displaying the hydrophobic character of a protein, J. Mol. Biol., 157: 105-132 (1982). The anti-MMP9 antibody had a GRAVY value of −0.40427, the anti-LOXL2 antibody had a GRAVY value of −0.38790, and the reference IgG4 antibody had a GRAVY value of −0.44909. This data demonstrates that all three IgG4 antibodies have similar hydrophobicity as determined by the GRAVY method, and suggests that the methods of the present application are likely to be effective on different IgG4 isotypes and/or antibodies with similar hydrophobic index. The methods of the present application may be applicable to a wide range of antibodies having different GRAVY values and/or hydrophobic indices other than those of the antibodies tested in these examples.

In another set of experiments, two cation-exchange multimodal resins, Capto MMC and Capto MMC ImpRes (both from GE Healthcare), demonstrated less than a 1 log reduction in HCP from approximately 600 ppm down to 175-210 ppm for both the bind and elute and the flow-through modes.

Example 2

In this example, a mixed mode chromatography was used as the final chromatography step as a finishing step employing a Capto adhere resin. Mixed mode chromatography can resolve product impurities with different sequences, such as fragments, elongated species, or Fc modified species. The mixed mode chromatography indicated removal of a unique peptide extension to C-terminus of antibody (elongated heterodimer impurity) with a mass difference of +1177 Da (SEQ ID NO: 1: EAEAASASELFQ). The mixed mode chromatography method could be employed as the final chromatography step to help remove a variety of impurities in addition to the +1177 Da peptide extension impurity removed in this Example.

from anion-exchange chromatography to multimodal anion-exchange chromatography employing Capto adhere resin. This modification to the polishing step was evaluated, as follows, for its ability to reduce the content of product-related impurities in the product pools.

Following the cation exchange chromatography step, a mixed mode chromatography step was performed using the Capto adhere anion exchange mixed-mode matrix available from GE Healthcare Life Sciences (Marlborough, Mass.). This mixed mode chromatography step using Capto adhere was compared to an anion exchange chromatography step using Capto Q. Experiments were performed using a variety of conditions comprising different pH values and conductivity. In some experiments using Capto adhere, the flow-through mode involved conditions where the pH varied from 6-8 and the conductivity was 5-20 mS/cm. In some experiments using Capto adhere, the bind and elute method involved conditions where the sample was loaded at a pH of 8.0 and a conductivity of 6-12 mS/cm, and elution was performed at a pH of 5.0+/−0.1 and a conductivity of 8-10 mS/cm. Product characterization of the mixed mode (Capto adhere) pools as compared to the pools generated from anion exchange (Capto Q) yielded a number of observations attributable to the use of Capto adhere.

The charge variant profile of the mixed mode (Capto adhere) pool was found to lack the most acidic variant peak that was present in the pool generated from anion exchange using Capto Q. This contributed to a reduction in the percentage of acidic peaks from 16.0% in the anion exchange (Capto Q) pool to 12.5% in the mixed mode (Capto adhere) pool. Table 4 provides the charge variant profile for process intermediates in the anti-MMP9 processes using either Capto adhere or Capto Q. The reduction in % acidic peaks observed in the Capto adhere pool was later found attributable to the reduction in Fc+1177 Da species observed in the Capto adhere pools, as discussed in more detail below.

TABLE 4

| Version | Run | % Acidic Peaks | % Main Peaks | % Basic Peaks |
|---|---|---|---|---|
| Mixed mode (Capto Adhere) | BI Run 3 MSS | 17.5 | 54.4 | 28.1 |
| | BI Run 3 Poros | 17.0 | 54.1 | 28.8 |
| | BI Run 3 Capto Adhere | 12.5 | 58.7 | 28.8 |
| | BI Run 3 UFDF | 12.4 | 58.6 | 29.0 |
| | BI Run 3 BDS | 12.0 | 55.5 | 32.5 |
| | Reference standard anti-MMP9 | 15.1 | 52.8 | 32.0 |
| Anion exchange (Capto Q) | BI Run 2 MSS | 17.0 | 53.7 | 29.3 |
| | BI Run 2 Poros | 17.1 | 54.6 | 28.3 |
| | BI Run 2 Capto Q | 16.0 | 55.9 | 28.1 |
| | BI Run 2 UFDF | 15.9 | 55.2 | 28.9 |
| | BI Run 2 BDS | 16.5 | 52.9 | 30.6 |
| | Reference standard anti-MMP9 | 15.1 | 52.8 | 32.1 |

Intact mass spectroscopy was used to analyze the intact and reduced heavy chain mass of the pools purified using the Capto Q and Capto adhere processes. Results from the pool purified by anion exchange (Capto Q) indicated the presence of a species with a mass difference of +1177 Da compared to the expected heavy chain sequence of the anti-MMP9 antibody. Further analysis revealed that the +1177 Da modification was due to a unique peptide extension on the C-terminus of the antibody consisting of the amino acid sequence EAEAASASELFQ (SEQ ID NO: 1). The observed intact and reduced MS data for the anti-MMP9 antibody is provided in Table 5.

TABLE 5

| | | Molecular Mass (Da) | | | | | |
|---|---|---|---|---|---|---|---|
| | | Intact | | Fc + 1177 Da | | Reduced | |
| BI Clinical Run | Process Version | G0F/G0F | G1F/G0F | C-Terminal Species | LC (1-214) | HC (1-441) G0F | HC (1-441) G1F |
| BI RUN 4 BDS | Mixed mode (Capto Adhere) | 146,823 | 146,986 | N/A | 23,398 | 50,027 | 50,188 |
| BI RUN 3 BDS | Mixed mode (Capto Adhere) | 146,822 | 146,985 | N/A | 23,398 | 50,026 | 50,189 |
| BI RUN 2 BDS | Anion exchange (Capto Q) | 146,823 | 146,985 | 148,001 | 23,399 | 50,027 | 50,189 |
| Reference standard anti-MMP9 | Anion exchange (Capto Q) | 146,824 | 146,985 | 148,002 | 23,400 | 50,028 | 50,189 |
| Theoretical mass (Da) | | 146,825 | 146,988 | 148,001 | 23,400 | 50,028 | 50,190 |

The observed intact mass matched the theoretical mass values for the anti-MMP9 antibody (see G0F and G1F/G0F columns in Table 5). The Fc+1177 Da species was observed in the material generated by the process using anion exchange (Capto Q) as the third chromatography step (Table 5, BI Run 2 BDS and Reference standard anti-MMP9), but was not observed in the material generated by the process using the mixed mode matrix (Capto adhere) (Table 5, BI Run 3 or 4 BDS). The observed reduced mass also matched the theoretical mass values (Table 5).

It was further demonstrated by reverse phase liquid chromatography that employing the mixed mode (Capto adhere) matrix in the polishing step removed the +1177 Da species containing the modified heavy chain. Pools generated by the mixed mode matrix (Capto adhere) and the anion exchange matrix (Capto Q) were treated with IdeS Protease, which cleaves intact antibodies into Fc and Fab$_2$ fragments. Reverse phase liquid chromatography was then used to identify the cleaved species present in each pool, including the presence or absence of the +1177 Da species. The +1177 Da species was observed as a peak at about 17.5 minutes in all BI Run 2 process intermediates generated using anion exchange (Capto Q). However, the +1177 Da species was absent from the process intermediates generated using the mixed mode polishing step (Capto adhere). This suggested that the Fc+1177 Da species was removed by use of Capto adhere.

These results suggest that the change in the ion exchange chromatography (IEC) profile exhibited by using the mixed mode (Capto adhere) polishing step as compared to the anion exchange (Capto Q) polishing step was attributed to the removal of the +1177 Da species.

Liquid chromatography mass spectrometry (LC-MS) analysis of the charge variant fractions was performed to determine whether the +1177 Da modified heavy chain contributes to the acidic region observed in the anion exchange (Capto Q) pool but not the mixed mode (Capto adhere) pool. A reference standard anti-MMP9 antibody was fractionated by IEC high-performance liquid chromatography (IEC-HPLC) into six peaks. These peaks appeared at about 13 minutes (Peak 1), about 13.75 minutes (Peak 2), about 15 minutes (Peak 3), about 16 minutes (Peak 4), about 17 minutes (Peak 5), and about 18.5 minutes (Peak 6). The acidic peaks included Peaks 1 and 2, and the basic peaks included Peaks 4, 5, and 6. Each fraction was collected and tested per tandem mass-spectrometry (MS/MS).

Extracted ion chromatography (EIC) was performed for each of the six IEC peaks that were fractioned. The full scan m/z for the +1177 Da species is $927.48^{2+}$. Peaks 1 and 2, which were shown to have elevated levels of +1177 Da species through IEC-HPLC and reversed phase HPLC (RP-HPLC) testing, also showed +1177 Da species in the EIC for the Peak 1 fraction and could be present in the Peak 2 fraction as well due to the relatively high abundance of a peak at 48.04 to 48.07 min present in the Peak 1 and Peak 2 fractions compared to the other fractions.

The MS/MS chromatograms demonstrated the +1177 Da species (m/z $927.48^{2+}$) was located in the Peak 1 fraction, and was also observed in the Peak 2 fraction. The +1177 Da species was not observed in any of the other fractions (i.e., Peaks 3, 4, 5, or 6). This data shows that the +1177 Da species was located within the acidic region of the charge variant assay and was the acidic variant of the anti-MMP9 antibody product.

An additional experiment was performed to confirm that the +1177 Da species corresponds to the first acidic peak of the charge variant profile. This was accomplished by enriching the +1177 Da species and comparing its charge profile to the charge profile of the reference standard anti-MMP9 antibody, which contains a first acidic peak along with some +1177 Da species. The +1177 Da species material was generated using the standard Capto adhere process through the low pH strip phase (0.1 M acetic acid, pH 3.0). Two additional washes (0.1 M ammonium acetate pH 4.5, 50 mM calcium chloride pH 4.5) were also performed sequentially after the low pH strip phase. All fractions were tested for +1177 Da species, but the 0.1 M acetic acid fraction (strip pool) was found to contain the highest level of +1177 Da species (28.5%+1177 Da for the 0.1 M acetic acid fraction versus 0.4%+1177 Da for the elution pool).

The +1177 Da species was further enriched by using the standard Capto adhere process by reloading the strip pool from capto adhere over the capto adhere and follow it with a typical capto adhere step elution, followed by an additional pH gradient strip phase. In other words, a post-elution pH gradient from pH 5.5 to pH 3.0 was used to separate the +1177 Da species from the native anti-MMP9 antibody product with more resolution than using the low pH strip phase alone. The fractions containing the higher levels of +1177 Da species were pooled together and measured for charge variants. The +1177 Da species enriched material showed a significant increase in the left most acidic peak in the charge variant profile compared to the charge variant profile of the reference standard anti-MMP9 antibody. The absorbance for the +1177 Da species non-enriched material was about 15 mAU at the retention time of about 10 mins. The enriched +1177 Da species had the absorbance of about 75mAU at the same retention time on the charge variant profile. The absorbance for the reference standard anti-MMP9 antibody was over 70 mAU. This confirmed that the Fc+1177 Da species is an acidic charge variant that could be detected in the charge variant profile.

Finally, application of mixed mode (Capto adhere) demonstrated complete removal of Fc+1177 Da modified species as confirmed by intact and reduced mass spectroscopy. This was observed even at levels of Fc+1177 Da species significantly higher than normal levels. For example, Capto adhere demonstrated complete removal of the +1177 Da species up to a tested 9-fold increase in Fc+1177 Da levels.

Example 3

The HCCF comprising anti-MMP9 antibody was loaded onto a protein A MSS matrix. The HCCF had an antibody titer of 2.55 g/L. A load density of 32.0 g-36.0 g anti-MMP9 antibody per liter of MSS resin has been established at 265-400 cm/hr loading. The wash solution used in the protein A chromatography step was 25 mM Tris, 500 mM NaCl at pH 7.7. Following a protein A chromatography step the eluate from the protein A column (Mabselect SuRe™ pool) was subject to low pH Viral inactivation. This pool was adjusted to pH of approximately 5.0 to 6.0 and was held at that pH for approximately 60 minutes. Thereafter, depth filtration was performed at 300 LMH (5 L/m²/min). Cygnus ELISA Version 3.0 was used for HCP analysis. In order to evaluate the impact of the filtration throughput and HCP levels in the filtrate pool, at each stage of filtration small volume samples (1 mL) were taken at multiple volumetric throughput points (50, 100, 150 and 200 L/m²) for HCP evaluation. The entire filtration was also analyzed for HCP levels as well. Exemplary results are shown in Table 6.

TABLE 6

| Pool Samples | HCP (ppm) | | |
| --- | --- | --- | --- |
| | Load | Pool | Reduction (%) |
| MabSelect SuRe pH 5 | 1391 | n/a | N/A |
| MabSelect SuRe adjusted to pH 6 | 1585 | n/a | N/A |
| 0.2 um Sterile Filtration only | | 1281 | 19% |
| C0HC | | 865 | 45% |
| C0HC→Emphaze | | 633 | 60% |
| C0HC→ X0HC | | 232 | 85% |

Example 4

In this Example, it was determined that the combination of increased urea at a concentration of 4 M to 6 M and reduced sodium chloride at a concentration of 0.5 M to 1.5 M in the wash buffer used in the protein A chromatography step resulted in a statistically significant reduction in half-antibody levels in the protein A chromatography pools. The combination of increased urea at a concentration of 4 M to 6 M and reduced sodium chloride at a concentration of 0.5 M to 1.5 M in the wash buffer could be employed to reduce the levels of a variety of product-related impurities, such as truncations and half-antibody forms.

During late stage process characterization, process parameters were studied in a multivariate fashion, where the impact of each process parameter on the process performance and product quality attributes was studied individually and also in combination with other product parameters. In these studies, the urea concentration level varied from 2 M to 6 M in combination with other parameters that were deemed significant on protein A purification. The impact of the urea concentration in combination with other parameters was evaluated based on product quality and process performance.

Half-antibody was measured and monitored with the non-reduced capillary electrophoresis (nrCE) as one of the product quality attributes in the protein A pools. Process parameters including protein A loading density, intermediate wash flowrate, urea concentration, sodium chloride concentration, along with load density, were shown to be statistically significant on the half-antibody levels in the elution pools.

Prediction profiles based on load density (g/L), wash flowrate (cm/hr), urea concentration (M), and sodium chloride concentration (M) were generated for half-antibody levels in the elution pools. The prediction profiles demonstrated that urea concentration seemed to be the factor that had the most significant impact on the half-antibody levels. It was observed that a higher urea concentration resulted in a lower level of half-antibody in the pool. Changing the urea concentration from 2 M to 6 M resulted in lowering the half-antibody level in the purified pool from 5.2% to 2.7%. In particular, the half-antibody level in the purified pool was 5.177% when the urea concentration was set at 2 M, the half-antibody level in the purified pool was 3.884% when the urea concentration was set at 4 M, and the half-antibody level in the purified pool was 2.6937% when the urea concentration was set at 6 M. The uncertainty in the Peak 2 (half-antibody) quantification was approximately +/−2.0% in the nrCE-SDS assay used. The model generated for half-antibody clearance in this study had an $r^2$ of 0.3, which indicated that the majority of variation in the half-antibody levels observed in this study could not be solely attributed to the wash buffer urea concentration alone. Thus, although the concentration of urea had a statistically significant impact on the levels of half-antibody in the pools, the model generated had a low predictive value ($r^2$=0.3). This indicated that other parameters that were not captured in the model had significant and relevant impact on the clearance of half-antibody species during the protein A wash using urea wash solution.

A follow-up study was conducted to assess the urea wash solution parameters of urea concentration and sodium chloride concentration, while fixing the loading/elution conditions to process parameter targets. Loading density was fixed at 28 g/L to provide a process-relevant higher loading condition, which would represent a challenge scenario for half-antibody clearance without impacting product recovery at target process conditions. Urea concentrations of 0 M, 2 M, 4 M, and 6 M, and sodium chloride concentrations of 0.5 M and 1.5 M were tested in all combinations to ascertain the statistical contribution of each to half-antibody clearance.

Half-antibody levels were tested with an improved non-reduced capillary electrophoresis-sodium dodecyl sulfate laser-induced fluorescence (nrCE-SDS LIF) assay with an improved uncertainty (<+/−1%) in the quantification of half-antibody. This provides greater certainty that the clearance levels of half-antibody can be attributed to the process parameters studied.

Univariate plots were generated showing the correlation of each process parameter/indicator with half-antibody levels as measured by LIF-nrCE-SDS. Exemplary results are provided in Table 7. It was observed that half-antibody clearance was improved when urea concentrations were increased at a concentration of 4 M to 6 M and when sodium chloride concentrations were less than 1.5 M, although this was accompanied by a slight reduction in process step yield. This suggests that the wash buffer with an increased concentration of urea in the range of 4 M to 6M and a reduced concentration of NaCl below 1.5 M in the range of 0.5 M to 1.5 M reduces hydrophobic interactions with the protein A, resulting in partial elution of the bound antibody and disproportionately more half-antibody species.

TABLE 7

| Urea (M) | NaCl (M) | Peak 2 Half mAb (%) | Yield (%) |
| --- | --- | --- | --- |
| 0 | 1.5 | 4.96 | 95.6 |
| 0 | 0.5 | 4.91 | 94.9 |
| 2 | 1.5 | 4.93 | 95.5 |
| 2 | 0.5 | 4.91 | 95.3 |
| 4 | 1.5 | 4.87 | 94.6 |
| 4 | 0.5 | 4.74 | 94.1 |
| 6 | 1.5 | 3.96 | 92.8 |
| 6 | 0.5 | 2.09 | 89.8 |

Two additional IgG4 antibodies were screened using wash solutions containing 0M, 4M, or 6M urea with a sodium chloride concentration of 0.5 M. Reduction of half antibody species was also observed at urea concentration of >4M for these antibodies. Exemplary results are provided in Table 8.

TABLE 8

| | Urea (M) | NaCl (M) | Peak 2 Half Mab (%) | Yield (%) |
| --- | --- | --- | --- | --- |
| anti-LOXL2 | 0 | 0.5 | 4.1 | 97.5 |
| anti-LOXL2 | 4 | 0.5 | 3.7 | 90.9 |

TABLE 8-continued

| | Urea (M) | NaCl (M) | Peak 2 Half Mab (%) | Yield (%) |
| --- | --- | --- | --- | --- |
| anti-LOXL2 | 6 | 0.5 | 1.2 | 82.9 |
| IgG4 control | 0 | 0.5 | 0.4 | 102.0 |
| IgG4 control | 4 | 0.5 | 0.4 | 98.6 |
| IgG4 control | 6 | 0.5 | 0.1 | 96.9 |

Comparison of the datasets for all three molecules showed that step yield is linearly correlated with the reduction in half-antibody levels for anti-MMP9, anti-LOXL2 and IgG4 control molecules ($r^2$=0.96, 0.87, and 0.64, respectively).

In summary, half-antibody clearance was determined to be significantly impacted by the wash solution composition and is highly correlated with the process step yield. The results show that urea concentration and sodium chloride concentration parameters had a significant impact on the process yield on protein A purification and that reduced process yield was highly correlated with half-antibody clearance over this process step. In addition, the process step yield is largely depressed by increasing the concentration of urea in the wash solution to a concentration greater than 4 M in the range of 4 M to 6 M.

Example 5

In this Example, it was determined that employing a pH gradient or multi-step elution to recover IgG1/IgG4 antibody products from protein A and protein L affinity resins can result in the partial resolution of half-antibody species and the ability to recover product with less than detectable half-antibody levels. This process can also be used in an iterative manner to enrich the half-antibody species greater than 10-fold from starting levels of less than 1.0%. The pH gradient or multi-step elution could be employed to reduce the levels of a variety of product-related impurities, such as misfolded antibody forms, aggregates, truncations, and half-antibody forms.

In some aspects, the downstream process for the anti-MMP9 process using Capto adhere consists of an affinity protein A chromatography step with a step elution using 40 mM acetic acid, pH 3.1. The elution step was modified to determine whether the levels of a product related impurity, such as half-antibody, could be further reduced. The elution step was modified to a gradient elution phase combining buffer A and buffer B at ratios from 0-100% buffer B (i.e., there is a gradual transition from 100% buffer A to 100% buffer B) over 20-30 column volumes (CV), or a multi-step elution phase at 50% buffer B, 60% buffer B, and 75% buffer B at 4 CV each. Buffer A consists of 25 mM sodium citrate, pH 5.0. Buffer B consists of 25 mM sodium citrate, pH 2.7. Both elution strategies (pH gradient elution and multi-step elution) can be utilized to recover up to 40% of loaded antibody in a half-antibody-depleted pool that contains less than detectable levels of half-antibody species.

Studies were performed to demonstrate that equivalent half-antibody clearance could be achieved using a representative sample of protein A resins including MabSelect (intact protein A ligand), MabSelect SuRe (recombinant Z-domain tetrameric ligand), and MabSelect SuRe pcc (smaller bead size, higher ligand coupling density). Capto L was also tested as an alternative antibody affinity resin that is also eluted at a low pH, but binds to a different region of the antibody (variable light (VL) domain for protein L versus predominantly CH2/CH3 domains for the protein A ligands).

Similar half-antibody resolution was achieved with two IgG4 antibody products (anti-MMP9 and anti-LOXL2 antibodies) and one IgG1 product (anti-GP120 antibody).

In most cases, the pH gradient studies were performed using the anti-MMP9 antibody product with a Capto Q virus filtration (VF) pool and formulated drug substance, which was diluted to 10 g/L using MabSelect SuRe equilibration buffer (25 mM Tris, 25 mM NaCl, pH 7.7). The initial experiments (Table 9, Experiments 1 to 4) utilized a loading density of 10 g/L on MabSelect, Capto L, MabSelect SuRe and MabSelect SuRe resins. This study indicated both affinity ligands were able to partially resolve half-antibody and monomeric species that MabSelect (Protein A ligand) was superior to Capto L (Protein L ligand) and resulted in improved peak resolution of half-antibody from monomer (0.21 compared to 0.10 for Capto L). The enrichment of half-antibody species was also higher for MabSelect with a maximum fold enrichment of 3.8 compared to a maximum fold enrichment of 2.2 for Capto L. The MabSelect SuRe resin was found to be superior to MabSelect, improving peak resolution to 0.33 and increasing the maximum fold enrichment of half-antibody species to 8.5. MabSelect SuRe and MabSelect SuRe pcc (smaller resin diameter) had equivalent resolution and half-antibody enrichment performance at a 10 g/L loading density. However, after increasing the loading density to 36 g/L, the peak resolution with MabSelect SuRe pcc (0.41) was now superior to MabSelect SuRe (0.28) and the maximum fold enrichment was also improved (2.5-fold compared to1.9-fold enrichment. This demonstrated that MabSelect SuRe pcc resin (smaller bead size) can achieve similar half-antibody peak resolution at 4-fold higher loading densities, which makes this a process-relevant option (Table 9, Experiment 6). While the half-antibody species appeared to be non-covalently associated to form a monoclonal antibody monomer at physiological pH, the results suggest that significant amounts of half-antibody remain dissociated at the low pH conditions of the elution phase. Therefore, utilizing gradient or multi-step low pH elution conditions could exploit avidity effects with both the protein A and protein L ligands.

Additional experiments demonstrated several more attributes of half-antibody clearance by pH gradient elution. MabSelect SuRe pcc resin with recombinant Z-domain protein A was used to resolve half-antibody species for two additional antibody products and two different IgG isotypes (anti-LOXL2, IgG4; and anti-GP120, IgG1) (Table 9, Experiments 7 and 8) at loading densities of 20 g/L. The initial half-antibody percentage was 5.1% for the anti-LOXL2 product and was 0.24% for the anti-GP120 product. The experiment using anti-LOXL2 IgG4 resulted in a peak resolution of 0.23 and a maximum fold enrichment of half-antibody species of 1.9 (Table 9, Experiment 7). The experiment using anti-GP120 IgG1 resulted in a peak resolution of 0.30 and a maximum fold enrichment of half-antibody species of 7.9 (Table 9, Experiment 8). This demonstrates that this pH gradient approach should be applicable to all IgG isotypes that bind to protein A ligands (IgG1/2/4). The data from the anti-GP120 experiment demonstrates that this approach has a tested range of applicability beginning from the lower limit of detection (LLOD) for starting half-antibody levels. Additionally, these separations were performed on antibody material loaded from harvested cell culture fluid. This demonstrates that the presence of the host-cell impurities does not impact the ability of protein A pH gradient elution to resolve half-antibody species.

Additional experiments demonstrated that superior resolution of half-antibody purification at loading densities of 20 g/L was achieved with MabSelect PrismA, which has a higher antibody binding capacity and modified ligand chemistry (Alkali-stable recombinant Z-domain protein A) as compared to MabSelect SuRe resins (Table 9, Experiments 9 and 10). MabSelect PrismA resin was used in separate experiments using anti-LOXL2 IgG4 or anti-GP120 IgG1 antibody products. The experiment using anti-LOXL2 IgG4 resulted in a peak resolution of 0.41, and generated a maximum fold enrichment of half-antibody species of 2.1 (Table 9, Experiment 9). The experiment using anti-GP120 resulted in a peak resolution of 0.30, and generated a maximum fold enrichment of half-antibody species of 9.5 (Table 9, Experiment 10). This further demonstrates the applicability of this approach to antibody affinity ligands with a pH-based mechanism for elution.

TABLE 9

| Experiment | Resin | Ligand Type | Antibody | Resin Diameter (μm) | Loading Density (g/L) resin | Initial Half mAb (%) | Max Fold Enrichment (x) | Baseline Peak Resolution between half-antibody and monomer species | % Product Recovery after removal of half-antibody species 10% removal | 50% removal | 90% removal |
|---|---|---|---|---|---|---|---|---|---|---|---|
| 1 | MabSelect | Protein A | Anti-MMP9 | 85 | 10 | 3.3 | 3.8 | 0.21 | 95 | 85 | 57 |
| 2 | Capto L | Protein L | Anti-MMP9 | 85 | 10 | 3.3 | 2.2 | 0.10 | 87 | 61 | 19 |
| 3 | MabSelect SuRe | Recombinant Z-domain protein A | Anti-MMP9 | 85 | 10 | 3.3 | 8.5 | 0.33 | 99 | 89 | 55 |
| 4 | MabSelect SuRe pcc | Recombinant Z-domain protein A | Anti-MMP9 | 50 | 10 | 3.3 | 8.7 | 0.30 | 95 | 87 | 57 |
| 5 | MabSelect SuRe | Recombinant Z-domain protein A | Anti-MMP9 | 85 | 36 | 3.3 | 1.9 | 0.28 | 89 | 51 | 11 |
| 6 | MabSelect SuRe pcc | Recombinant Z-domain protein A | Anti-MMP9 | 50 | 36 | 3.3 | 2.5 | 0.41 | 90 | 49 | 11 |
| 7 | MabSelect SuRe pcc | Recombinant Z-domain protein A | Anti-LOXL2 | 50 | 20 | 5.1 | 1.9 | 0.23 | Not Determined | Not Determined | Not Determined |

TABLE 9-continued

| Experiment | Resin | Ligand Type | Antibody | Resin Diameter (μm) | Loading Density (g/L) resin | Initial Half mAb (%) | Max Fold Enrichment (x) | Baseline Peak Resolution between half-antibody and monomer species | % Product Recovery after removal of half-antibody species | | |
|---|---|---|---|---|---|---|---|---|---|---|---|
| | | | | | | | | | 10% removal | 50% removal | 90% removal |
| 8 | MabSelect PrismA | Recombinant Z-domain protein A | Anti-LOXL2 | 60 | 20 | 5.1 | 2.1 | 0.41 | Not Determined | Not Determined | Not Determined |
| 9 | MabSelect SuRe pcc | Recombinant Z-domain protein A | Anti-GP120 | 50 | 20 | 0.24 | 7.9 | 0.30 | Not Determined | Not Determined | Not Determined |
| 10 | MabSelect PrismA | Alkali-stable recombinant Z-domain protein A | Anti-GP120 | 60 | 20 | 0.24 | 9.5 | 0.30 | Not Determined | Not Determined | Not Determined |

In another set of experiments, the anti-MMP9 antibody product was processed through three successive cycles of pH gradient elution (Table 10). The first cycle had 3.4% initial half-antibody and had a 9.5% recovery of half-antibody (2.8× max fold enrichment). The second cycle had 10.3% initial half-antibody and had a 22.2% recovery of half-antibody (2.2× max fold enrichment). The third cycle had 32.5% initial half-antibody and had a 45.7% recovery of half-antibody (1.4× max fold enrichment). The loading density for all three cycles was 40 g/L. The results demonstrated that the process can resolve half-antibody species from starting levels of about 3-33% half-antibody with decreasing efficiency at higher purity levels of half-antibody.

TABLE 10

| Resin | Molecule | Loading Density (g/L resin) | Initial Half mAb (%) | Highest Half Mab Purity Recovered (%) | Max Fold Enrichment (x) |
|---|---|---|---|---|---|
| MabSelect SuRe | IgG4 - A | 40 | 3.4 | 9.5 | 2.8 |
| MabSelect SuRe | IgG4 - A | 40 | 10.3 | 22.2 | 2.2 |
| MabSelect SuRe | IgG4 - A | 40 | 32.5 | 45.7 | 1.4 |

Collectively, data from Tables 9 and 10 demonstrate that this approach has a tested range of applicability from the lower limit of deletion (LLOD) to 32.5% starting half-antibody levels.

In summary, this Example demonstrated that pH gradient-based elution can partially resolve half-antibody species and reduce their levels to undetectable levels with greater than 40% recovery. This can be accomplished with a variety of antibody affinity ligands (e.g., protein A, recombinant Z-domain tetramer, protein L, recombinant alkali-stable Z-domain hexamer), with different IgG isotypes (IgG1, IgG4) and antibody products (e.g., anti-MMP9, anti-LOXL2, anti-GP120), from different levels of impurities (HCCF, purified process intermediate pools), different intermediate wash steps (anti-MMP9 processes using wash buffers with Capto Q or Capto adhere), and with different levels of starting half-antibody (LLOD to 32.5%) with no loss in resolution performance. Decreasing bead size and increasing binding capacity were both found to be beneficial in improving both the resolution of pH gradient separations and the maximum loading density, thus improving the process throughout.

TABLE 11

| SEQ ID NO: | Amino Acid Sequence | Description |
|---|---|---|
| 1 | EAEAASASELFQ | Peptide |
| 2 | MAVLVLFLCLVAFPSCVLSQVQLKESGPGLVAPSQSLSITCTVSG FSLLSYGVHWVRQPPGKGLEWLGVIWTGGTTNYNSALMSRLSISK DDSKSQVFLKMNSLQTDDTAIYYCARYYYGMDYWGQGTSVTVSSA KTTPPSVYPLAPGCGDTTGSSVTLGCLVKGYFPESVTVTWNSGSL SSSVHTFPALLQSGLYTMSSSVTVPSSTWPSQTVTCSVAHPASST TVDKKLEPSGPISTINPCPPCKECHKCPAPNLEGGPSVFIFPPNI KDVLMISLTPKVTCVVVDVSEDDPDVRISWFVNNVEVHTAQTQTH REDYNSTIRVVSALPIQHQDWMSGKEFKCKVNNKDLPSPIERTIS KIKGLVRAPQVYILPPPAEQLSRKDVSLTCLVVGFNPGDISVEWT SNGHTEENYKDTAPVLDSDGSYFIYSKLDIKTSKWEKTDSFSCNV RHEGLKNYYLKKTISRSPGK | Heavy chain |
| 3 | MESQIQVFVFVFLWLSGVDGDIVMTQSHKFMSTSVGDRVSITCKA SQDVRNTVAWYQQKTGQSPKLLIYSSSYRNTGVPDRFTGSGSGTD FTFTISSVQAEDLAVYFCQQHYITPYTFGGGTKLEIKRADAAPTV SIFPPSSEQLTSGGASVVCFLNNFYPKDINVKWKIDGSERQNGVL NSWTDQDSKDSTYSMSSTLTLTKDEYERHNSYTCEATHKTSTSPI VKSFNRNEC | Light chain |
| 4 | QVQLKESGPGLVAPSQSLSITCTVSGFSLLSYGVHWVRQPPGKGL EWLGVIWTGGTTNYNSALMSRLSISKDDSKSQVFLKMNSLQTDDT AIYYCARYYYGMDYWGQGTSVTVSS | Variable heavy chain |

TABLE 11-continued

| SEQ ID NO: | Amino Acid Sequence | Description |
|---|---|---|
| 5 | DIVMTQSHKFMSTSVGDRVSITCKASQDVRNTVAWYQQKTGQSPK LLIYSSSYRNTGVPDRFTGSGSGTDFTFTISSVQAEDLAVYFCQQ HYITPYTFGGGTKLEIK | Variable light chain |
| 6 | QVQLQESGPGLVKPSETLSLTCTVSGFSLLSYGVHWVRQPPGKGL EWLGVIWTGGTTNYNSALMSRLTISKDDSKSTVYLKMNSLKTEDT AIYYCARYYYGMDYWGQGTSVTVSS | Variable heavy chain |
| 7 | QVQLQESGPGLVKPSETLSLTCTVSGFSLLSYGVHWVRQPPGKGL EWLGVIWTGGTTNYNSALMSRLTISKDDSKNTVYLKMNSLKTEDT AIYYCARYYYGMDYWGQGTLVTVSS | Variable heavy chain |
| 8 | QVQLQESGPGLVKPSETLSLTCTVSGFSLLSYGVHWVRQPPGKGL EWLGVIWTGGTTNYNSALMSRFTISKDDSKNTVYLKMNSLKTEDT AIYYCARYYYGMDYWGQGTLVTVSS | Variable heavy chain |
| 9 | QVQLQESGPGLVKPSETLSLTCTVSGFSLLSYGVHWVRQPPGKGL EWLGVIWTGGTTNYNSALMSRFTISKDDSKNTLYLKMNSLKTEDT AIYYCARYYYGMDYWGQGTLVTVSS | Variable heavy chain |
| 10 | DIVMTQSPSFLSASVGDRVTITCKASQDVRNTVAWYQQKTGKAPK LLIYSSSYRNTGVPDRFTGSGSGTDFTLTISSLQAEDVAVYFCQQ HYITPYTFGGGTKVEIK | Variable light chain |
| 11 | DIVMTQSPSSLSASVGDRVTITCKASQDVRNTVAWYQQKPGKAPK LLIYSSSYRNTGVPDRFTGSGSGTDFTLTISSLQAEDVAVYFCQQ HYITPYTFGGGTKVEIK | Variable light chain |
| 12 | DIQMTQSPSSLSASVGDRVTITCKASQDVRNTVAWYQQKPGKAPK LLIYSSSYRNTGVPDRFSGSGSGTDFTLTISSLQAEDVAVYFCQQ HYITPYTFGGGTKVEIK | Variable light chain |
| 13 | DIQMTQSPSSLSASVGDRVTITCKASQDVRNTVAWYQQKPGKAPK LLIYSSSYRNTGVPDRFSGSGSGTDFTLTISSLQAEDVAVYYCQQ HYITPYTFGGGTKVEIK | Variable light chain |
| 14 | GFSLLSYGVH | CDR1 of heavy chain |
| 15 | VIWTGGTTNYNSALMS | CDR2 of heavy chain |
| 16 | YYYGMDY | CDR3 of heavy chain |
| 17 | KASQDVRNTVA | CDR1 of light chain |
| 18 | SSSYRNT | CDR2 of light chain |
| 19 | QQHYITPYT | CDR3 of light chain |
| 20 | MAVLVLFLCLVAFPSCVLSQVQLKESGPGLVAPSQSLSITCTVSG FSLLSYGVHWVRQPPGKGLEWLGVIWTGGSTNYNSALMSRLSISK DDSKSQVFLKMNSLQTDDTAMYYCARYYYAMDYWGQGTSVTVSSA KTTPPSVYPLAPGCGDTTGSSVTLGCLVKGYFPESVTVTWNSGSL SSSVHTFPALLQSGLYTMSSSVTVPSSTWPSQTVTCSVAHPASST TVDKKLEPSGPISTINPCPPCKECHKCPAPNLEGGPSVFIFPPNI KDVLMISLTPKVTCVVVDVSEDDPDVRISWFVNNVEVHTAQTQTH REDYNSTIRVVSALPIQHQDWMSGKEFKCKVNNKDLPSPIERTIS KIKGLVRAPQVYILPPPAEQLSRKDVSLTCLVVGFNPGDISVEWT SNGHTEENYKDTAPVLDSDGSYFIYSKLDIKTSKWEKTDSFSCNV RHEGLKNYYLKKTISRSPGK | Heavy chain |
| 21 | MESQIQVFVFVFLWLSGVDGDIVMTQSHKFMFTSVGDRVSITCKA SQDVRNTVAWYQQKTGQSPKLLIYSASYRNTGVPDRFTGSISGTD FTFTISSVQAEDLALYYCQQHYSTPYTFGGGTKLEVKRADAAPTV SIFPPSSEQLTSGGASVVCFLNNFYPKDINVKWKIDGSERQNGVL NSWTDQDSKDSTYSMSSTLTLTKDEYERHNSYTCEATHKTSTSPI VKSFNRNEC | Light chain |
| 22 | QVQLKESGPGLVAPSQSLSITCTVSGFSLLSYGVHWVRQPPGKGL EWLGVIWTGGSTNYNSALMSRLSISKDDSKSQVFLKMNSLQTDDT AMYYCARYYYAMDYWGQGTSVTVSS | Variable heavy chain |

TABLE 11-continued

| SEQ ID NO: | Amino Acid Sequence | Description |
|---|---|---|
| 23 | DIVMTQSHKFMFTSVGDRVSITCKASQDVRNTVAWYQQKTGQSPK LLIYSASYRNTGVPDRFTGSISGTDFTFTISSVQAEDLALYYCQQ HYSTPYTFGGGTKLEVK | Variable light chain |
| 24 | GFSLLSYGVH | CDR1 of heavy chain |
| 25 | VIWTGGSTNYNSALMS | CDR2 of heavy chain |
| 26 | YYYAMDY | CDR3 of heavy chain |
| 27 | KASQDVRNTVA | CDR1 of light chain |
| 28 | SASYRNT | CDR2 of light chain |
| 29 | QQHYSTPYT | CDR3 of light chain |
| 30 | QVFVYMLLWLSGVDGDIVMTQSQKFMSTSVGDRVSVTCKASQNVG TNVAWYQQKPGQSPKALIYSASYRFSGVPDRFTGSGSGTDFTLTI SNVQSEDLAEYFCQQYNSYPYTFGGGTKLEIKRADAAPTVSIFPP SSEQLTSGGASVVCFLNNFYPKDINVKWKIDGSERQNGVLNSWTD QDSKDSTYSMSSTLTLTKDEYERHNSYTCEATHKTSTSPIVKSFN RNEC | Light chain |
| 31 | DIVMTQSQKFMSTSVGDRVSVTCKASQNVGTNVAWYQQKPGQSPK ALIYSASYRFSGVPDRFTGSGSGTDFTLTISNVQSEDLAEYFCQQ YNSYPYTFGGGTKLEIK | Variable light chain |
| 32 | KASQNVGTNVA | CDR1 of light chain |
| 33 | SASYRFS | CDR2 of light chain |
| 34 | QQYNSYPYT | CDR3 of light chain |
| 35 | MSSAQFLGLLLLCFQGTRCDIQMTQTTSSLSASLGDRVTISCSAS QGISNYLNWYQQKPDGTFKLLIYYTSILHSGVPSRFSGSGSGTDY SLTISNLEPEDIATYYCQQYGWLPRTFGGGTKLEIKRADAAPTVS IFPPSSEQLTSGGASVVCFLNNFYPKDINVKWKIDGSERQNGVLN SWTDQDSKDSTYSMSSTLTLTKDEYERHNSYTCEATHKTSTSPIV KSFNRNEC | Light chain |
| 36 | MGWSSIILFLVATATGVHSQVQLQQPGSVLVRPGASVKLSCTASG YTFTSYWMNWVKQRPGQGLEWIGETYPISGRTNYNEKFKVKATLT VDTSSSTAYMDLNSLTSEDSAVYYCARSRANWDDYWGQGTTLTVS SAKTTPPSVYPLAPGSAAQTNSMVTLGCLVKGYFPEPVTVTWNSG SLSSGVHTFPAVLQSDLYTLSSSVTVPSSTWPSETVTCNVAHPAS STKVDKKIVPRDCGCKPCICTVPEVSSVFIFPPKPKDVLTITLTP KVTCVVVDISKDDPEVQFSWFVDDVEVHTAQTQPREEQFNSTFRS VSELPIMHQDWLNGKEFKCRVNSAAFPAPIEKTISKTKGRPKAPQ VYTIPPPKEQMAKDKVSLTCMITDFFPEDITVEWQWNGQPAENYK NTQPIMDTDGSYFVYSKLNVQKSNWEAGNTFTCSVLHEGLHNHEI TEKSLSHSPGK | Heavy chain |
| 37 | QVQLQQPGSVLVRPGASVKLSCTASGYTFTSYWMNWVKQRPGQGL EWIGEIYPISGRTNYNEKFKVKATLTVDTSSSTAYMDLNSLTSED SAVYYCARSRANWDDYWGQGTTLTVSS | Variable heavy chain |
| 38 | DIQMTQTTSSLSASLGDRVTISCSASQGISNYLNWYQQKPDGTFK LLIYYTSILHSGVPSRFSGSGSGTDYSLTISNLEPEDIATYYCQQ YGWLPRTFGGGTKLEIK | Variable light chain |
| 39 | GYTFTSYWMN | CDR1 of heavy chain |
| 40 | EIYPISGRTNYNEKFKV | CDR2 of heavy chain |
| 41 | SRANWDDY | CDR3 of heavy chain |

TABLE 11-continued

| SEQ ID NO: | Amino Acid Sequence | Description |
|---|---|---|
| 42 | SASQGISNYLN | CDR1 of light chain |
| 43 | YTSILHS | CDR2 of light chain |
| 44 | QQYGWLPRT | CDR3 of light chain |
| 45 | MGWSLILLFLVAVATRVHSQVQLQESGPGLVKPSETLSLTCTVSG FSLLSYGVHWVRQPPGKGLEWLGVIWTGTTNYNSALMSRFTISK DDSKNTVYLKMNSLKTEDTAIYYCARYYYGMDYWGQGTLVTVSSA STKGPSVFPLAPCSRSTSESTAALGCLVKDYFPEPVTVSWNSGAL TSGVHTFPAVLQSSGLYSLSSVVTVPSSSLGTKTYTCNVDHKPSN TKVDKRVESKYGPPCPPCPAPEFLGGPSVFLFPPKPKDTLMISRT PEVTCVVVDVSQEDPEVQFNWYVDGVEVHNAKTKPREEQFNSTYR VVSVLTVLHQDWLNGKEYKCKVSNKGLPSSIEKTISKAKGQPREP QVYTLPPSQEEMTKNQVSLTCLVKGFYPSDIAVEWESNGQPENNY KTTPPVLDSDGSFFLYSRLTVDKSRWQEGNVFSCSVMHEALHNHY TQKSLSLSLGK | Heavy chain |
| 46 | MRVPAQLLGLLLLWLPGARCDIQMTQSPSSLSASVGDRVTITCKA SQDVRNTVAWYQQKPGKAPKLLIYSSSYRNTGVPDRFSGSGSGTD FTLTISSLQAEDVAVYYCQQHYITPYTFGGGTKVEIKRTVAAPSV FIFPPSDEQLKSGTASVVCLLNNFYPREAKVQWKVDNALQSGNSQ ESVTEQDSKDSTYSLSSTLTLSKADYEKHKVYACEVTHQGLSSPV TKSFNRGEC | Light chain |
| 47 | MEWSRVFIFLLSVTAGVHSQVQLQQSGAELVRPGTSVKVSCKASG YAFTYYLIEWVKQRPGQGLEWIGVINPGSGGTNYNEKFKGKATLT ADKSSSTAYMQLSSLTSDDSAVYFCARNWMNFDYWGQGTTLTVSS | Variable heavy chain |
| 48 | MRCLAEFLGLLVLWIPGAIGDIVMTQAAPSVSVTPGESVSISCRS SKSLLHSNGNTYLYWFLQRPGQSPQFLIYRMSNLASGVPDRFSGS GSGTAFTLRISRVEAEDVGVYYCMQHLEYPYTFGGGTKLEIK | Variable light chain |
| 49 | MGWSLILLFLVAVATRVHSQVQLVQSGAEVKKPGASVKVSCKASG YAFTYYLIEWVRQAPGQGLEWIGVINPGSGGTNYNEKFKGRATIT ADKSTSTAYMELSSLRSEDTAVYFCARNWMNFDYWGQGTTVTVSS ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLFPPKPKDTLMISR TPEVTCVVVDVSQEDPEVQFNWYVDGVEVHNAKTKPREEQFNSTY RVVSVLTVLHQDWLNGKEYKCKVSNKGLPSSIEKTISKAKGQPRE PQVYTLPPSQEEMTKNQVSLTCLVKGFYPSDIAVEWESNGQPENN YKTTPPVLDSDGSFFLYSRLTVDKSRWQEGNVFSCSVMHEALHNH YTQKSLSLSLGK | Variable heavy chain |
| 50 | MRVPAQLLGLLLLWLPGARCDIVMTQTPLSLSVTPGQPASISCRS SKSLLHSNGNTYLYWFLQKPGQSPQFLIYRMSNLASGVPDRFSGS GSGTDFTLKISRVEAEDVGVYYCMQHLEYPYTFGGGTKVEIKRTV AAPSVFIFPPSDEQLKSGTASVVCLLNNFYPREAKVQWKVDNALQ SGNSQESVTEQDSKDSTYSLSSTLTLSKADYEKHKVYACEVTHQG LSSPVTKSFNRGEC | Variable light chain |

What is claimed is:

1. A method for purifying, producing, processing, or isolating an antibody from a mixture comprising the antibody, the method comprising:
   a) loading the mixture onto protein A chromatography;
   b) washing the chromatography with at least one wash solution, wherein the at least one wash solution comprises from about 4000 mM to about 8000 mM urea; and
   c) eluting with an elution buffer to obtain the antibody.

2. The method of claim 1, wherein the at least one wash solution further comprises arginine, guanidine, sodium chloride (NaCl), caprylate, or combination thereof.

3. The method of claim 2, wherein the at least one wash solution comprises from about 100 mM to 1000 mM arginine, from about 500 mM to about 1000 mM guanidine, from about 500 mM to about 1500 mM NaCl, from about 1 mM to about 50 mM caprylate, or combination thereof.

4. The method of claim 1, wherein the at least one wash solution is at a pH from about 5.0 to about 8.5.

5. The method of claim 1, wherein the elution buffer comprises from about 5 mM to about 65 mM acetic acid.

6. The method of claim 1, wherein the elution buffer is at a pH of about 2.5 to about 3.5.

7. The method of claim 1, wherein the washing step is carried out at a flow rate of about 50 cm/hr to about 400 cm/hr.

8. The method of claim 1, wherein the washing step is repeated at least one, two, three, or four times.

9. The method of claim 1, further comprising viral inactivation.

10. The method of claim 9, wherein the viral inactivation is conducted at a pH below 4.0 for at least 30 minutes.

11. The method of claim 1, further comprising depth filtration, membrane filtration, a cation exchange chromatography, a mixed-mode chromatography, ultrafiltration, diafiltration, or combination thereof.

12. The method of claim 1, further comprising a filtering step using depth filtration, wherein the depth filtration comprises a depth filter selected from the group consisting of a COHC depth filter, a XOHC depth filter, a synthetic hybrid depth filter, or combinations thereof.

13. The method of claim 1, further comprising analyzing at least one impurity.

14. The method of claim 1, whereby the method results in the antibody that is substantially free of at least one impurity.

15. The method of claim 1, wherein the antibody is selected from the group consisting of an anti-lysyl oxidase like 2 (LOXL2) antibody and an anti-metalloproteinase 9 (MMP9) antibody.

16. The method of claim 1, wherein the antibody comprises the sequences selected from the group consisting of SEQ ID NOs: 2, 3, 4, 5, 8, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

17. A method for producing, purifying, processing, or isolating an antibody from a host cell culture fluid comprising the antibody, the method comprising:
   a) loading the host cell culture fluid onto a protein A or protein L chromatography to obtain a loaded matrix;
   b) washing the loaded matrix with at least one urea wash solution, wherein the at least one urea wash solution comprises from about 4000 mM to about 8000 mM urea to obtain a protein A purified antibody or protein L purified antibody; and
   c) subjecting a protein A purified antibody or protein L purified antibody to a pH gradient-based elution or a multi-step elution to obtain the antibody.

18. The method of claim 17, wherein the host cell culture fluid is loaded onto protein A chromatography; wherein the at least one urea wash solution comprises from about 4000 mM to about 6000 mM urea and from about 500 mM to about 1500 mM NaCl and is at a pH of about 7.7 to about 8.2.

19. The method of claim 17, further comprising filtering the protein A purified antibody by depth filtration, wherein the depth filtration comprises a depth filter selected from the group consisting of a COHC depth filter, a XOHC depth filter, a synthetic hybrid depth filter or combinations thereof.

* * * * *

SEQUENCE LISTING

<160> NUMBER OF SEQ ID NOS: 50

<210> SEQ ID NO 1
<211> LENGTH: 12
<212> TYPE: PRT
<213> ORGANISM: Artificial Sequence
<220> FEATURE:
<223> OTHER INFORMATION: 1177 Da extension

<400> SEQUENCE: 1

Glu Ala Glu Ala Ala Ser Ala Ser Glu Leu Phe Gln
1               5                   10

<210> SEQ ID NO 2

```
<211> LENGTH: 470
<212> TYPE: PRT
<213> ORGANISM: Mus musculus
<220> FEATURE:
<221> NAME/KEY: CHAIN
<222> LOCATION: (1)..(470)
<223> OTHER INFORMATION: AB0041 heavy chain
<220> FEATURE:
<221> NAME/KEY: PEPTIDE
<222> LOCATION: (1)..(19)
<223> OTHER INFORMATION: signal peptide
<220> FEATURE:
<221> NAME/KEY: VARIANT
<222> LOCATION: (135)..(470)
<223> OTHER INFORMATION: IgG2b constant region

<400> SEQUENCE: 2
```

Met Ala Val Leu Val Leu Phe Leu Cys Leu Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Leu Ser Tyr Gly Val His Trp Val Arg Gln Pro Pro Gly Lys Gly Leu
    50                  55                  60

Glu Trp Leu Gly Val Ile Trp Thr Gly Gly Thr Thr Asn Tyr Asn Ser
65                  70                  75                  80

Ala Leu Met Ser Arg Leu Ser Ile Ser Lys Asp Asp Ser Lys Ser Gln
                85                  90                  95

Val Phe Leu Lys Met Asn Ser Leu Gln Thr Asp Asp Thr Ala Ile Tyr
            100                 105                 110

Tyr Cys Ala Arg Tyr Tyr Tyr Gly Met Asp Tyr Trp Gly Gln Gly Thr
        115                 120                 125

Ser Val Thr Val Ser Ser Ala Lys Thr Thr Pro Pro Ser Val Tyr Pro
    130                 135                 140

Leu Ala Pro Gly Cys Gly Asp Thr Thr Gly Ser Ser Val Thr Leu Gly
145                 150                 155                 160

Cys Leu Val Lys Gly Tyr Phe Pro Glu Ser Val Thr Val Thr Trp Asn
                165                 170                 175

Ser Gly Ser Leu Ser Ser Ser Val His Thr Phe Pro Ala Leu Leu Gln
            180                 185                 190

Ser Gly Leu Tyr Thr Met Ser Ser Ser Val Thr Val Pro Ser Ser Thr
        195                 200                 205

Trp Pro Ser Gln Thr Val Thr Cys Ser Val Ala His Pro Ala Ser Ser
210                 215                 220

Thr Thr Val Asp Lys Lys Leu Glu Pro Ser Gly Pro Ile Ser Thr Ile
225                 230                 235                 240

Asn Pro Cys Pro Pro Cys Lys Glu Cys His Lys Cys Pro Ala Pro Asn
                245                 250                 255

Leu Glu Gly Gly Pro Ser Val Phe Ile Phe Pro Pro Asn Ile Lys Asp
            260                 265                 270

Val Leu Met Ile Ser Leu Thr Pro Lys Val Thr Cys Val Val Val Asp
        275                 280                 285

Val Ser Glu Asp Asp Pro Asp Val Arg Ile Ser Trp Phe Val Asn Asn
    290                 295                 300

Val Glu Val His Thr Ala Gln Thr Gln Thr His Arg Glu Asp Tyr Asn
305                 310                 315                 320

Ser Thr Ile Arg Val Val Ser Ala Leu Pro Ile Gln His Gln Asp Trp

```
                        325                 330                 335
Met Ser Gly Lys Glu Phe Lys Cys Lys Val Asn Asn Lys Asp Leu Pro
                340                 345                 350

Ser Pro Ile Glu Arg Thr Ile Ser Lys Ile Lys Gly Leu Val Arg Ala
            355                 360                 365

Pro Gln Val Tyr Ile Leu Pro Pro Ala Glu Gln Leu Ser Arg Lys
        370                 375                 380

Asp Val Ser Leu Thr Cys Leu Val Val Gly Phe Asn Pro Gly Asp Ile
385                 390                 395                 400

Ser Val Glu Trp Thr Ser Asn Gly His Thr Glu Glu Asn Tyr Lys Asp
                405                 410                 415

Thr Ala Pro Val Leu Asp Ser Asp Gly Ser Tyr Phe Ile Tyr Ser Lys
                420                 425                 430

Leu Asp Ile Lys Thr Ser Lys Trp Glu Lys Thr Asp Ser Phe Ser Cys
                435                 440                 445

Asn Val Arg His Glu Gly Leu Lys Asn Tyr Tyr Leu Lys Lys Thr Ile
                450                 455                 460

Ser Arg Ser Pro Gly Lys
465                 470

<210> SEQ ID NO 3
<211> LENGTH: 234
<212> TYPE: PRT
<213> ORGANISM: Mus musculus
<220> FEATURE:
<221> NAME/KEY: CHAIN
<222> LOCATION: (1)..(234)
<223> OTHER INFORMATION: AB0041 light chain
<220> FEATURE:
<221> NAME/KEY: PEPTIDE
<222> LOCATION: (1)..(20)
<223> OTHER INFORMATION: signal peptide
<220> FEATURE:
<221> NAME/KEY: VARIANT
<222> LOCATION: (128)..(234)
<223> OTHER INFORMATION: kappa constant region

<400> SEQUENCE: 3

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
                20                  25                  30

Thr Ser Val Gly Asp Arg Val Ser Ile Thr Cys Lys Ala Ser Gln Asp
            35                  40                  45

Val Arg Asn Thr Val Ala Trp Tyr Gln Gln Lys Thr Gly Gln Ser Pro
        50                  55                  60

Lys Leu Leu Ile Tyr Ser Ser Tyr Arg Asn Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Phe Cys Gln Gln His Tyr
                100                 105                 110

Ile Thr Pro Tyr Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160
```

```
Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 4
<211> LENGTH: 115
<212> TYPE: PRT
<213> ORGANISM: Mus musculus
<220> FEATURE:
<221> NAME/KEY: CHAIN
<222> LOCATION: (1)..(115)
<223> OTHER INFORMATION: variable region of the IgG2b heavy chain of
      AB0041
<220> FEATURE:
<221> NAME/KEY: VARIANT
<222> LOCATION: (26)..(35)
<223> OTHER INFORMATION: complementarity-determining region (CDR)
<220> FEATURE:
<221> NAME/KEY: VARIANT
<222> LOCATION: (50)..(65)
<223> OTHER INFORMATION: complementarity-determining region (CDR)
<220> FEATURE:
<221> NAME/KEY: VARIANT
<222> LOCATION: (98)..(104)
<223> OTHER INFORMATION: complementarity-determining region (CDR)

<400> SEQUENCE: 4

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Leu Ser Ile Ser Lys Asp Asp Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Arg Tyr Tyr Tyr Gly Met Asp Tyr Trp Gly Gln Gly Thr Ser Val Thr
            100                 105                 110

Val Ser Ser
        115

<210> SEQ ID NO 5
<211> LENGTH: 107
<212> TYPE: PRT
<213> ORGANISM: Mus musculus
<220> FEATURE:
<221> NAME/KEY: CHAIN
<222> LOCATION: (1)..(107)
<223> OTHER INFORMATION: variable region of the kappa light chain of
      AB0041
<220> FEATURE:
<221> NAME/KEY: VARIANT
<222> LOCATION: (24)..(34)
<223> OTHER INFORMATION: complementarity-determining region (CDR)
<220> FEATURE:
```

```
<221> NAME/KEY: VARIANT
<222> LOCATION: (50)..(56)
<223> OTHER INFORMATION: complementarity-determining region (CDR)
<220> FEATURE:
<221> NAME/KEY: VARIANT
<222> LOCATION: (89)..(97)
<223> OTHER INFORMATION: complementarity-determining region (CDR)

<400> SEQUENCE: 5

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Asn Thr
            20                  25                  30

Val Ala Trp Tyr Gln Gln Lys Thr Gly Gln Ser Pro Lys Leu Leu Ile
        35                  40                  45

Tyr Ser Ser Ser Tyr Arg Asn Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Phe Cys Gln Gln His Tyr Ile Thr Pro Tyr
                85                  90                  95

Thr Phe Gly Gly Gly Thr Lys Leu Glu Ile Lys
            100                 105

<210> SEQ ID NO 6
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(115)
<223> OTHER INFORMATION: VH1 heavy chain variant

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Leu Thr Ile Ser Lys Asp Asp Ser Lys Ser Thr Val Tyr Leu
65                  70                  75                  80

Lys Met Asn Ser Leu Lys Thr Glu Asp Thr Ala Ile Tyr Tyr Cys Ala
                85                  90                  95

Arg Tyr Tyr Tyr Gly Met Asp Tyr Trp Gly Gln Gly Thr Ser Val Thr
            100                 105                 110

Val Ser Ser
        115

<210> SEQ ID NO 7
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(115)
```

<223> OTHER INFORMATION: VH2 heavy chain variant

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Leu Thr Ile Ser Lys Asp Asp Ser Lys Asn Thr Val Tyr Leu
65                  70                  75                  80

Lys Met Asn Ser Leu Lys Thr Glu Asp Thr Ala Ile Tyr Tyr Cys Ala
                85                  90                  95

Arg Tyr Tyr Tyr Gly Met Asp Tyr Trp Gly Gln Gly Thr Leu Val Thr
            100                 105                 110

Val Ser Ser
        115

<210> SEQ ID NO 8
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(115)
<223> OTHER INFORMATION: VH3 heavy chain variant

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Phe Thr Ile Ser Lys Asp Asp Ser Lys Asn Thr Val Tyr Leu
65                  70                  75                  80

Lys Met Asn Ser Leu Lys Thr Glu Asp Thr Ala Ile Tyr Tyr Cys Ala
                85                  90                  95

Arg Tyr Tyr Tyr Gly Met Asp Tyr Trp Gly Gln Gly Thr Leu Val Thr
            100                 105                 110

Val Ser Ser
        115

<210> SEQ ID NO 9
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(115)
<223> OTHER INFORMATION: VH4 heavy chain variant

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Phe Thr Ile Ser Lys Asp Asp Ser Lys Asn Thr Leu Tyr Leu
65              70                  75                  80

Lys Met Asn Ser Leu Lys Thr Glu Asp Thr Ala Ile Tyr Tyr Cys Ala
                85                  90                  95

Arg Tyr Tyr Tyr Gly Met Asp Tyr Trp Gly Gln Gly Thr Leu Val Thr
            100                 105                 110

Val Ser Ser
        115

<210> SEQ ID NO 10
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(107)
<223> OTHER INFORMATION: Vk1 light chain variant

<400> SEQUENCE: 10

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Arg Asn Thr
            20                  25                  30

Val Ala Trp Tyr Gln Gln Lys Thr Gly Lys Ala Pro Lys Leu Leu Ile
        35                  40                  45

Tyr Ser Ser Ser Tyr Arg Asn Thr Gly Val Pro Asp Arg Phe Thr Gly
    50                  55                  60

Ser Gly Ser Gly Thr Asp Phe Thr Leu Thr Ile Ser Ser Leu Gln Ala
65              70                  75                  80

Glu Asp Val Ala Val Tyr Phe Cys Gln Gln His Tyr Ile Thr Pro Tyr
                85                  90                  95

Thr Phe Gly Gly Gly Thr Lys Val Glu Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(107)
<223> OTHER INFORMATION: Vk2 light chain variant

<400> SEQUENCE: 11

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Thr
            20                  25                  30

Val Ala Trp Tyr Gln Gln Lys Pro Gly Lys Ala Pro Lys Leu Leu Ile
            35                  40                  45

Tyr Ser Ser Ser Tyr Arg Asn Thr Gly Val Pro Asp Arg Phe Thr Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln His Tyr Ile Thr Pro Tyr
                85                  90                  95

Thr Phe Gly Gly Gly Thr Lys Val Glu Ile Lys
            100                 105

<210> SEQ ID NO 12
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(107)
<223> OTHER INFORMATION: Vk3 light chain variant

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Thr
            20                  25                  30

Val Ala Trp Tyr Gln Gln Lys Pro Gly Lys Ala Pro Lys Leu Leu Ile
            35                  40                  45

Tyr Ser Ser Ser Tyr Arg Asn Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln His Tyr Ile Thr Pro Tyr
                85                  90                  95

Thr Phe Gly Gly Gly Thr Lys Val Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(107)
<223> OTHER INFORMATION: Vk4 light chain variant

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Thr
            20                  25                  30

Val Ala Trp Tyr Gln Gln Lys Pro Gly Lys Ala Pro Lys Leu Leu Ile
            35                  40                  45

Tyr Ser Ser Ser Tyr Arg Asn Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Ile Thr Pro Tyr
            85                  90                  95

Thr Phe Gly Gly Gly Thr Lys Val Glu Ile Lys
            100                 105

<210> SEQ ID NO 14
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(10)
<223> OTHER INFORMATION: complementarity-determining region (CDR1) of
      heavy chain of anti-MMP9 antibody

<400> SEQUENCE: 14

Gly Phe Ser Leu Leu Ser Tyr Gly Val His
1               5                   10

<210> SEQ ID NO 15
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(16)
<223> OTHER INFORMATION: complementarity-determining region (CDR2) of
      heavy chain of anti-MMP9 antibody

<400> SEQUENCE: 15

Val Ile Trp Thr Gly Gly Thr Thr Asn Tyr Asn Ser Ala Leu Met Ser
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(7)
<223> OTHER INFORMATION: complementarity-determining region (CDR3) of
      heavy chain of anti-MMP9 antibody

<400> SEQUENCE: 16

Tyr Tyr Tyr Gly Met Asp Tyr
1               5

<210> SEQ ID NO 17
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(11)
<223> OTHER INFORMATION: complementarity-determining region (CDR1) of
      light chain of anti-MMP9 antibody

<400> SEQUENCE: 17

Lys Ala Ser Gln Asp Val Arg Asn Thr Val Ala
1               5                   10

```
<210> SEQ ID NO 18
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(7)
<223> OTHER INFORMATION: complementarity-determining region (CDR2) of
      light chain of anti-MMP9 antibody

<400> SEQUENCE: 18

Ser Ser Ser Tyr Arg Asn Thr
1               5

<210> SEQ ID NO 19
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)..(9)
<223> OTHER INFORMATION: complementarity-determining region (CDR3) of
      light chain of anti-MMP9 antibody

<400> SEQUENCE: 19

Gln Gln His Tyr Ile Thr Pro Tyr Thr
1               5

<210> SEQ ID NO 20
<211> LENGTH: 470
<212> TYPE: PRT
<213> ORGANISM: Mus musculus
<220> FEATURE:
<221> NAME/KEY: CHAIN
<222> LOCATION: (1)..(470)
<223> OTHER INFORMATION: M4 heavy chain (IgG2b)

<400> SEQUENCE: 20

Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Leu Ser Tyr Gly Val His Trp Val Arg Gln Pro Pro Gly Lys Gly Leu
    50                  55                  60

Glu Trp Leu Gly Val Ile Trp Thr Gly Gly Ser Thr Asn Tyr Asn Ser
65                  70                  75                  80

Ala Leu Met Ser Arg Leu Ser Ile Ser Lys Asp Asp Ser Lys Ser Gln
                85                  90                  95

Val Phe Leu Lys Met Asn Ser Leu Gln Thr Asp Asp Thr Ala Met Tyr
            100                 105                 110

Tyr Cys Ala Arg Tyr Tyr Tyr Ala Met Asp Tyr Trp Gly Gln Gly Thr
        115                 120                 125

Ser Val Thr Val Ser Ser Ala Lys Thr Thr Pro Pro Ser Val Tyr Pro
    130                 135                 140

Leu Ala Pro Gly Cys Gly Asp Thr Thr Gly Ser Ser Val Thr Leu Gly
145                 150                 155                 160

Cys Leu Val Lys Gly Tyr Phe Pro Glu Ser Val Thr Val Thr Trp Asn
```

```
                        165                 170                 175
Ser Gly Ser Leu Ser Ser Val His Thr Phe Pro Ala Leu Leu Gln
            180                 185                 190

Ser Gly Leu Tyr Thr Met Ser Ser Val Thr Val Pro Ser Ser Thr
            195                 200                 205

Trp Pro Ser Gln Thr Val Thr Cys Ser Val Ala His Pro Ala Ser Ser
            210                 215                 220

Thr Thr Val Asp Lys Lys Leu Glu Pro Ser Gly Pro Ile Ser Thr Ile
225                 230                 235                 240

Asn Pro Cys Pro Pro Cys Lys Glu Cys His Lys Cys Pro Ala Pro Asn
                245                 250                 255

Leu Glu Gly Gly Pro Ser Val Phe Ile Phe Pro Pro Asn Ile Lys Asp
                260                 265                 270

Val Leu Met Ile Ser Leu Thr Pro Lys Val Thr Cys Val Val Val Asp
                275                 280                 285

Val Ser Glu Asp Asp Pro Asp Val Arg Ile Ser Trp Phe Val Asn Asn
            290                 295                 300

Val Glu Val His Thr Ala Gln Thr Gln Thr His Arg Glu Asp Tyr Asn
305                 310                 315                 320

Ser Thr Ile Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
                340                 345                 350

Ser Pro Ile Glu Arg Thr Ile Ser Lys Ile Lys Gly Leu Val Arg Ala
            355                 360                 365

Pro Gln Val Tyr Ile Leu Pro Pro Ala Glu Gln Leu Ser Arg Lys
            370                 375                 380

Asp Val Ser Leu Thr Cys Leu Val Val Gly Phe Asn Pro Gly Asp Ile
385                 390                 395                 400

Ser Val Glu Trp Thr Ser Asn Gly His Thr Glu Glu Asn Tyr Lys Asp
                405                 410                 415

Thr Ala Pro Val Leu Asp Ser Asp Gly Ser Tyr Phe Ile Tyr Ser Lys
            420                 425                 430

Leu Asp Ile Lys Thr Ser Lys Trp Glu Lys Thr Asp Ser Phe Ser Cys
            435                 440                 445

Asn Val Arg His Glu Gly Leu Lys Asn Tyr Tyr Leu Lys Lys Thr Ile
            450                 455                 460

Ser Arg Ser Pro Gly Lys
465                 470

<210> SEQ ID NO 21
<211> LENGTH: 234
<212> TYPE: PRT
<213> ORGANISM: Mus musculus
<220> FEATURE:
<221> NAME/KEY: CHAIN
<222> LOCATION: (1)..(234)
<223> OTHER INFORMATION: M4 light chain (kappa)

<400> SEQUENCE: 21

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Phe
            20                  25                  30

Thr Ser Val Gly Asp Arg Val Ser Ile Thr Cys Lys Ala Ser Gln Asp
            35                  40                  45
```

-continued

```
Val Arg Asn Thr Val Ala Trp Tyr Gln Gln Lys Thr Gly Gln Ser Pro
 50                  55                  60

Lys Leu Leu Ile Tyr Ser Ala Ser Tyr Arg Asn Thr Gly Val Pro Asp
 65                  70                  75                  80

Arg Phe Thr Gly Ser Ile Ser Gly Thr Asp Phe Thr Phe Thr Ile Ser
                 85                  90                  95

Ser Val Gln Ala Glu Asp Leu Ala Leu Tyr Tyr Cys Gln Gln His Tyr
            100                 105                 110

Ser Thr Pro Tyr Thr Phe Gly Gly Gly Thr Lys Leu Glu Val Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 22
<211> LENGTH: 115
<212> TYPE: PRT
<213> ORGANISM: Mus musculus

<400> SEQUENCE: 22

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Leu Ser Tyr
                20                  25                  30

Gly Val His Trp Val Arg Gln Pro Pro Gly Lys Gly Leu Glu Trp Leu
            35                  40                  45

Gly Val Ile Trp Thr Gly Gly Ser Thr Asn Tyr Asn Ser Ala Leu Met
        50                  55                  60

Ser Arg Leu Ser Ile Ser Lys Asp Asp Ser Lys Ser Gln Val Phe Leu
 65                  70                  75                  80

Lys Met Asn Ser Leu Gln Thr Asp Asp Thr Ala Met Tyr Tyr Cys Ala
                 85                  90                  95

Arg Tyr Tyr Tyr Ala Met Asp Tyr Trp Gly Gln Gly Thr Ser Val Thr
            100                 105                 110

Val Ser Ser
        115

<210> SEQ ID NO 23
<211> LENGTH: 107
<212> TYPE: PRT
<213> ORGANISM: Mus musculus

<400> SEQUENCE: 23

Asp Ile Val Met Thr Gln Ser His Lys Phe Met Phe Thr Ser Val Gly
 1               5                  10                  15
```

Asp Arg Val Ser Ile Thr Cys Lys Ala Ser Gln Asp Val Arg Asn Thr
            20                  25                  30

Val Ala Trp Tyr Gln Lys Thr Gly Gln Ser Pro Lys Leu Leu Ile
        35                  40                  45

Tyr Ser Ala Ser Tyr Arg Asn Thr Gly Val Pro Asp Arg Phe Thr Gly
    50                  55                  60

Ser Ile Ser Gly Thr Asp Phe Thr Phe Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Val Lys
            100                 105

<210> SEQ ID NO 24
<211> LENGTH: 10
<212> TYPE: PRT
<213> ORGANISM: Mus musculus

<400> SEQUENCE: 24

Gly Phe Ser Leu Leu Ser Tyr Gly Val His
1               5                   10

<210> SEQ ID NO 25
<211> LENGTH: 16
<212> TYPE: PRT
<213> ORGANISM: Mus musculus

<400> SEQUENCE: 25

Val Ile Trp Thr Gly Gly Ser Thr Asn Tyr Asn Ser Ala Leu Met Ser
1               5                   10                  15

<210> SEQ ID NO 26
<211> LENGTH: 7
<212> TYPE: PRT
<213> ORGANISM: Mus musculus

<400> SEQUENCE: 26

Tyr Tyr Tyr Ala Met Asp Tyr
1               5

<210> SEQ ID NO 27
<211> LENGTH: 11
<212> TYPE: PRT
<213> ORGANISM: Mus musculus

<400> SEQUENCE: 27

Lys Ala Ser Gln Asp Val Arg Asn Thr Val Ala
1               5                   10

<210> SEQ ID NO 28
<211> LENGTH: 7
<212> TYPE: PRT
<213> ORGANISM: Mus musculus

<400> SEQUENCE: 28

Ser Ala Ser Tyr Arg Asn Thr
1               5

<210> SEQ ID NO 29
<211> LENGTH: 9
<212> TYPE: PRT
<213> ORGANISM: Mus musculus

<400> SEQUENCE: 29

Gln Gln His Tyr Ser Thr Pro Tyr Thr
1               5

<210> SEQ ID NO 30
<211> LENGTH: 229
<212> TYPE: PRT
<213> ORGANISM: Mus musculus
<220> FEATURE:
<221> NAME/KEY: CHAIN
<222> LOCATION: (1)..(229)
<223> OTHER INFORMATION: M12 kappa chain

<400> SEQUENCE: 30

Gln Val Phe Val Tyr Met Leu Leu Trp Leu Ser Gly Val Asp Gly Asp
1               5                   10                  15

Ile Val Met Thr Gln Ser Gln Lys Phe Met Ser Thr Ser Val Gly Asp
            20                  25                  30

Arg Val Ser Val Thr Cys Lys Ala Ser Gln Asn Val Gly Thr Asn Val
        35                  40                  45

Ala Trp Tyr Gln Gln Lys Pro Gly Gln Ser Pro Lys Ala Leu Ile Tyr
    50                  55                  60

Ser Ala Ser Tyr Arg Phe Ser Gly Val Pro Asp Arg Phe Thr Gly Ser
65                  70                  75                  80

Gly Ser Gly Thr Asp Phe Thr Leu Thr Ile Ser Asn Val Gln Ser Glu
                85                  90                  95

Asp Leu Ala Glu Tyr Phe Cys Gln Gln Tyr Asn Ser Tyr Pro Tyr Thr
            100                 105                 110

Phe Gly Gly Gly Thr Lys Leu Glu Ile Lys Arg Ala Asp Ala Ala Pro
        115                 120                 125

Thr Val Ser Ile Phe Pro Pro Ser Glu Gln Leu Thr Ser Gly Gly
    130                 135                 140

Ala Ser Val Val Cys Phe Leu Asn Asn Phe Tyr Pro Lys Asp Ile Asn
145                 150                 155                 160

Val Lys Trp Lys Ile Asp Gly Ser Glu Arg Gln Asn Gly Val Leu Asn
                165                 170                 175

Ser Trp Thr Asp Gln Asp Ser Lys Asp Ser Thr Tyr Ser Met Ser Ser
            180                 185                 190

Thr Leu Thr Leu Thr Lys Asp Glu Tyr Glu Arg His Asn Ser Tyr Thr
        195                 200                 205

Cys Glu Ala Thr His Lys Thr Ser Thr Ser Pro Ile Val Lys Ser Phe
    210                 215                 220

Asn Arg Asn Glu Cys
225

<210> SEQ ID NO 31
<211> LENGTH: 107
<212> TYPE: PRT
<213> ORGANISM: Mus musculus

<400> SEQUENCE: 31

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

```
Tyr Ser Ala Ser Tyr Arg Phe Ser Gly Val Pro Asp Arg Phe Thr Gly
        50                  55                  60

Ser Gly Ser Gly Thr Asp Phe Thr Leu Thr Ile Ser Asn Val Gln Ser
 65              70                  75                  80

Glu Asp Leu Ala Glu Tyr Phe Cys Gln Gln Tyr Asn Ser Tyr Pro Tyr
                 85                  90                  95

Thr Phe Gly Gly Gly Thr Lys Leu Glu Ile Lys
                100                 105
```

<210> SEQ ID NO 32
<211> LENGTH: 11
<212> TYPE: PRT
<213> ORGANISM: Mus musculus

<400> SEQUENCE: 32

```
Lys Ala Ser Gln Asn Val Gly Thr Asn Val Ala
 1               5                  10
```

<210> SEQ ID NO 33
<211> LENGTH: 7
<212> TYPE: PRT
<213> ORGANISM: Mus musculus

<400> SEQUENCE: 33

```
Ser Ala Ser Tyr Arg Phe Ser
 1               5
```

<210> SEQ ID NO 34
<211> LENGTH: 9
<212> TYPE: PRT
<213> ORGANISM: Mus musculus

<400> SEQUENCE: 34

```
Gln Gln Tyr Asn Ser Tyr Pro Tyr Thr
 1               5
```

<210> SEQ ID NO 35
<211> LENGTH: 233
<212> TYPE: PRT
<213> ORGANISM: Mus musculus
<220> FEATURE:
<221> NAME/KEY: CHAIN
<222> LOCATION: (1)..(233)
<223> OTHER INFORMATION: AB0046 kappa light chain

<400> SEQUENCE: 35

```
Met Ser Ser Ala Gln Phe Leu Gly Leu Leu Leu Cys Phe Gln Gly
 1               5                  10                  15

Thr Arg Cys Asp Ile Gln Met Thr Gln Thr Thr Ser Ser Leu Ser Ala
                20                  25                  30

Ser Leu Gly Asp Arg Val Thr Ile Ser Cys Ser Ala Ser Gln Gly Ile
            35                  40                  45

Ser Asn Tyr Leu Asn Trp Tyr Gln Gln Lys Pro Asp Gly Thr Phe Lys
         50                  55                  60

Leu Leu Ile Tyr Tyr Thr Ser Ile Leu His Ser Gly Val Pro Ser Arg
 65                  70                  75                  80

Phe Ser Gly Ser Gly Ser Gly Thr Asp Tyr Ser Leu Thr Ile Ser Asn
                 85                  90                  95

Leu Glu Pro Glu Asp Ile Ala Thr Tyr Tyr Cys Gln Gln Tyr Gly Trp
                100                 105                 110
```

```
Leu Pro Arg Thr Phe Gly Gly Thr Lys Leu Glu Ile Lys Arg Ala
            115                 120                 125
Asp Ala Ala Pro Thr Val Ser Ile Phe Pro Pro Ser Glu Gln Leu
        130                 135                 140
Thr Ser Gly Gly Ala Ser Val Val Cys Phe Leu Asn Asn Phe Tyr Pro
145                 150                 155                 160
Lys Asp Ile Asn Val Lys Trp Lys Ile Asp Gly Ser Glu Arg Gln Asn
                165                 170                 175
Gly Val Leu Asn Ser Trp Thr Asp Gln Asp Ser Lys Asp Ser Thr Tyr
            180                 185                 190
Ser Met Ser Ser Thr Leu Thr Leu Thr Lys Asp Glu Tyr Glu Arg His
            195                 200                 205
Asn Ser Tyr Thr Cys Glu Ala Thr His Lys Thr Ser Thr Ser Pro Ile
            210                 215                 220
Val Lys Ser Phe Asn Arg Asn Glu Cys
225                 230

<210> SEQ ID NO 36
<211> LENGTH: 460
<212> TYPE: PRT
<213> ORGANISM: Mus musculus
<220> FEATURE:
<221> NAME/KEY: CHAIN
<222> LOCATION: (1)..(460)
<223> OTHER INFORMATION: AB0046 IgG1 heavy chain

<400> SEQUENCE: 36

Met Gly Trp Ser Ser Ile Ile Leu Phe Leu Val Ala Thr Ala Thr Gly
1               5                   10                  15
Val His Ser Gln Val Gln Leu Gln Gln Pro Gly Ser Val Leu Val Arg
                20                  25                  30
Pro Gly Ala Ser Val Lys Leu Ser Cys Thr Ala Ser Gly Tyr Thr Phe
            35                  40                  45
Thr Ser Tyr Trp Met Asn Trp Val Lys Gln Arg Pro Gly Gln Gly Leu
50                  55                  60
Glu Trp Ile Gly Glu Ile Tyr Pro Ile Ser Gly Arg Thr Asn Tyr Asn
65                  70                  75                  80
Glu Lys Phe Lys Val Lys Ala Thr Leu Thr Val Asp Thr Ser Ser Ser
                85                  90                  95
Thr Ala Tyr Met Asp Leu Asn Ser Leu Thr Ser Glu Asp Ser Ala Val
            100                 105                 110
Tyr Tyr Cys Ala Arg Ser Arg Ala Asn Trp Asp Asp Tyr Trp Gly Gln
            115                 120                 125
Gly Thr Thr Leu Thr Val Ser Ser Ala Lys Thr Thr Pro Pro Ser Val
130                 135                 140
Tyr Pro Leu Ala Pro Gly Ser Ala Ala Gln Thr Asn Ser Met Val Thr
145                 150                 155                 160
Leu Gly Cys Leu Val Lys Gly Tyr Phe Pro Glu Pro Val Thr Val Thr
                165                 170                 175
Trp Asn Ser Gly Ser Leu Ser Ser Gly Val His Thr Phe Pro Ala Val
            180                 185                 190
Leu Gln Ser Asp Leu Tyr Thr Leu Ser Ser Ser Val Thr Val Pro Ser
            195                 200                 205
Ser Thr Trp Pro Ser Glu Thr Val Thr Cys Asn Val Ala His Pro Ala
            210                 215                 220
Ser Ser Thr Lys Val Asp Lys Lys Ile Val Pro Arg Asp Cys Gly Cys
```

```
            225                 230                 235                 240
Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
                260                 265                 270

Thr Cys Val Val Val Asp Ile Ser Lys Asp Asp Pro Glu Val Gln Phe
                275                 280                 285

Ser Trp Phe Val Asp Asp Val Glu Val His Thr Ala Gln Thr Gln Pro
            290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
                340                 345                 350

Lys Gly Arg Pro Lys Ala Pro Gln Val Tyr Thr Ile Pro Pro Pro Lys
                355                 360                 365

Glu Gln Met Ala Lys Asp Lys Val Ser Leu Thr Cys Met Ile Thr Asp
            370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
                420                 425                 430

Gly Asn Thr Phe Thr Cys Ser Val Leu His Glu Gly Leu His Asn His
                435                 440                 445

His Thr Glu Lys Ser Leu Ser His Ser Pro Gly Lys
            450                 455                 460

<210> SEQ ID NO 37
<211> LENGTH: 117
<212> TYPE: PRT
<213> ORGANISM: Mus musculus

<400> SEQUENCE: 37

Gln Val Gln Leu Gln Gln Pro Gly Ser Val Leu Val Arg Pro Gly Ala
1               5                   10                  15

Ser Val Lys Leu Ser Cys Thr Ala Ser Gly Tyr Thr Phe Thr Ser Tyr
                20                  25                  30

Trp Met Asn Trp Val Lys Gln Arg Pro Gly Gln Gly Leu Glu Trp Ile
            35                  40                  45

Gly Glu Ile Tyr Pro Ile Ser Gly Arg Thr Asn Tyr Asn Glu Lys Phe
        50                  55                  60

Lys Val Lys Ala Thr Leu Thr Val Asp Thr Ser Ser Ser Thr Ala Tyr
65                  70                  75                  80

Met Asp Leu Asn Ser Leu Thr Ser Glu Asp Ser Ala Val Tyr Tyr Cys
                85                  90                  95

Ala Arg Ser Arg Ala Asn Trp Asp Asp Tyr Trp Gly Gln Gly Thr Thr
                100                 105                 110

Leu Thr Val Ser Ser
            115

<210> SEQ ID NO 38
<211> LENGTH: 107
```

```
<212> TYPE: PRT
<213> ORGANISM: Mus musculus

<400> SEQUENCE: 38

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Phe Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Gly Trp Leu Pro Arg
                85                  90                  95

Thr Phe Gly Gly Gly Thr Lys Leu Glu Ile Lys
            100                 105

<210> SEQ ID NO 39
<211> LENGTH: 10
<212> TYPE: PRT
<213> ORGANISM: Mus musculus
<220> FEATURE:
<223> OTHER INFORMATION: CDR1 heavy chain AB0046

<400> SEQUENCE: 39

Gly Tyr Thr Phe Thr Ser Tyr Trp Met Asn
1               5                   10

<210> SEQ ID NO 40
<211> LENGTH: 17
<212> TYPE: PRT
<213> ORGANISM: Mus musculus
<220> FEATURE:
<223> OTHER INFORMATION: CDR2 heavy chain AB0046

<400> SEQUENCE: 40

Glu Ile Tyr Pro Ile Ser Gly Arg Thr Asn Tyr Asn Glu Lys Phe Lys
1               5                   10                  15

Val

<210> SEQ ID NO 41
<211> LENGTH: 8
<212> TYPE: PRT
<213> ORGANISM: Mus musculus
<220> FEATURE:
<223> OTHER INFORMATION: CDR3 heavy chain AB0046

<400> SEQUENCE: 41

Ser Arg Ala Asn Trp Asp Asp Tyr
1               5

<210> SEQ ID NO 42
<211> LENGTH: 11
<212> TYPE: PRT
<213> ORGANISM: Mus musculus
<220> FEATURE:
<223> OTHER INFORMATION: CDR1 light chain AB0046

<400> SEQUENCE: 42

Ser Ala Ser Gln Gly Ile Ser Asn Tyr Leu Asn
1               5                   10
```

<210> SEQ ID NO 43
<211> LENGTH: 7
<212> TYPE: PRT
<213> ORGANISM: Mus musculus
<220> FEATURE:
<223> OTHER INFORMATION: CDR2 light chain AB0046

<400> SEQUENCE: 43

Tyr Thr Ser Ile Leu His Ser
1               5

<210> SEQ ID NO 44
<211> LENGTH: 9
<212> TYPE: PRT
<213> ORGANISM: Mus musculus
<220> FEATURE:
<223> OTHER INFORMATION: CDR3 light chain AB0046

<400> SEQUENCE: 44

Gln Gln Tyr Gly Trp Leu Pro Arg Thr
1               5

<210> SEQ ID NO 45
<211> LENGTH: 461
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)..(461)
<223> OTHER INFORMATION: AB0045 heavy chain

<400> SEQUENCE: 45

Met Gly Trp Ser Leu Ile Leu Leu Phe Leu Val Ala Val Ala Thr Arg
1               5                   10                  15

Val His Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Leu Ser Tyr Gly Val His Trp Val Arg Gln Pro Pro Gly Lys Gly Leu
    50                  55                  60

Glu Trp Leu Gly Val Ile Trp Thr Gly Gly Thr Thr Asn Tyr Asn Ser
65                  70                  75                  80

Ala Leu Met Ser Arg Phe Thr Ile Ser Lys Asp Asp Ser Lys Asn Thr
                85                  90                  95

Val Tyr Leu Lys Met Asn Ser Leu Lys Thr Glu Asp Thr Ala Ile Tyr
            100                 105                 110

Tyr Cys Ala Arg Tyr Tyr Tyr Gly Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Lys Thr Tyr Thr Cys Asn Val Asp His Lys Pro Ser
            210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
            275                 280                 285

Phe Asn Trp Tyr Val Asp Gly Val Glu Val His Asn Ala Lys Thr Lys
            290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Gln Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
            420                 425                 430

Glu Gly Asn Val Phe Ser Cys Ser Val Met His Glu Ala Leu His Asn
            435                 440                 445

His Tyr Thr Gln Lys Ser Leu Ser Leu Ser Leu Gly Lys
            450                 455                 460

<210> SEQ ID NO 46
<211> LENGTH: 234
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)..(234)
<223> OTHER INFORMATION: AB0045 light chain

<400> SEQUENCE: 46

Met Arg Val Pro Ala Gln Leu Leu Gly Leu Leu Leu Leu Trp Leu Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Arg Asn Thr Val Ala Trp Tyr Gln Gln Lys Pro Gly Lys Ala Pro
50                  55                  60

Lys Leu Leu Ile Tyr Ser Ser Ser Tyr Arg Asn Thr Gly Val Pro Asp
65                  70                  75                  80

Arg Phe Ser Gly Ser Gly Ser Gly Thr Asp Phe Thr Leu Thr Ile Ser

```
                85                  90                  95
Ser Leu Gln Ala Glu Asp Val Ala Val Tyr Tyr Cys Gln Gln His Tyr
            100                 105                 110

Ile Thr Pro Tyr Thr Phe Gly Gly Gly Thr Lys Val Glu Ile Lys Arg
            115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 47
<211> LENGTH: 135
<212> TYPE: PRT
<213> ORGANISM: Mus musculus
<220> FEATURE:
<223> OTHER INFORMATION: VH chain AB0023

<400> SEQUENCE: 47

Met Glu Trp Ser Arg Val Phe Ile Phe Leu Leu Ser Val Thr Ala Gly
1               5                   10                  15

Val His Ser Gln Val Gln Leu Gln Gln Ser Gly Ala Glu Leu Val Arg
            20                  25                  30

Pro Gly Thr Ser Val Lys Val Ser Cys Lys Ala Ser Gly Tyr Ala Phe
        35                  40                  45

Thr Tyr Tyr Leu Ile Glu Trp Val Lys Gln Arg Pro Gly Gln Gly Leu
    50                  55                  60

Glu Trp Ile Gly Val Ile Asn Pro Gly Ser Gly Gly Thr Asn Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Asp Asp Ser Ala Val
            100                 105                 110

Tyr Phe Cys Ala Arg Asn Trp Met Asn Phe Asp Tyr Trp Gly Gln Gly
            115                 120                 125

Thr Thr Leu Thr Val Ser Ser
            130                 135

<210> SEQ ID NO 48
<211> LENGTH: 132
<212> TYPE: PRT
<213> ORGANISM: Mus musculus
<220> FEATURE:
<223> OTHER INFORMATION: VL chain AB0023

<400> SEQUENCE: 48

Met Arg Cys Leu Ala Glu Phe Leu Gly Leu Leu Val Leu Trp Ile Pro
1               5                   10                  15
```

```
Gly Ala Ile Gly Asp Ile Val Met Thr Gln Ala Ala Pro Ser Val Ser
                20                  25                  30

Val Thr Pro Gly Glu Ser Val Ser Ile Ser Cys Arg Ser Ser Lys Ser
            35                  40                  45

Leu Leu His Ser Asn Gly Asn Thr Tyr Leu Tyr Trp Phe Leu Gln Arg
    50                  55                  60

Pro Gly Gln Ser Pro Gln Phe Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys
    130
```

<210> SEQ ID NO 49
<211> LENGTH: 462
<212> TYPE: PRT
<213> ORGANISM: Mus musculus
<220> FEATURE:
<223> OTHER INFORMATION: VH chain AB0024

<400> SEQUENCE: 49

```
Met Gly Trp Ser Leu Ile Leu Leu Phe Leu Val Ala Val Ala Thr Arg
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Ala Phe
            35                  40                  45

Thr Tyr Tyr Leu Ile Glu Trp Val Arg Gln Ala Pro Gly Gln Gly Leu
    50                  55                  60

Glu Trp Ile Gly Val Ile Asn Pro Gly Ser Gly Gly Thr Asn Tyr Asn
65                  70                  75                  80

Glu Lys Phe Lys Gly Arg Ala Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Phe Cys Ala Arg Asn Trp Met Asn Phe Asp Tyr Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240
```

```
Cys Pro Pro Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys
    450                 455                 460

<210> SEQ ID NO 50
<211> LENGTH: 239
<212> TYPE: PRT
<213> ORGANISM: Mus musculus
<220> FEATURE:
<223> OTHER INFORMATION: VL chain AB0024

<400> SEQUENCE: 50

Met Arg Val Pro Ala Gln Leu Leu Gly Leu Leu Leu Trp Leu Pro
1               5                   10                  15

Gly Ala Arg Cys Asp Ile Val Met Thr Gln Thr Pro Leu Ser Leu Ser
            20                  25                  30

Val Thr Pro Gly Gln Pro Ala Ser Ile Ser Cys Arg Ser Ser Lys Ser
        35                  40                  45

Leu Leu His Ser Asn Gly Asn Thr Tyr Leu Tyr Trp Phe Leu Gln Lys
    50                  55                  60

Pro Gly Gln Ser Pro Gln Phe Leu Ile Tyr Arg Met Ser Asn Leu Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Val Glu Ile Lys Arg Thr Val Ala Ala Pro Ser Val Phe Ile Phe Pro
    130                 135                 140
```

```
Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235
```